United States Patent [19]
Lerner et al.

[11] Patent Number: 5,840,332
[45] Date of Patent: Nov. 24, 1998

[54] GASTROINTESTINAL DRUG DELIVERY SYSTEM

[75] Inventors: E. Itzhak Lerner; Moshe Flashner, both of Petah Tikva; Adel Penhasi, Bat-Yam, all of Israel

[73] Assignee: Perio Products Ltd., Jerusalem, Israel

[21] Appl. No.: 588,247

[22] Filed: Jan. 18, 1996

[51] Int. Cl.$^6$ .................................................... A61K 9/20
[52] U.S. Cl. .................... 424/464; 424/489; 424/480; 424/495; 424/488; 494/486; 494/487
[58] Field of Search .................................. 424/464, 489, 424/480, 457, 468, 495; 128/260

[56] References Cited

U.S. PATENT DOCUMENTS

| | | | |
|---|---|---|---|
| 3,845,770 | 11/1974 | Theeuwes et al. | 128/260 |
| 3,916,899 | 11/1975 | Theeuwes et al. | 128/260 |
| 3,921,636 | 11/1975 | Zaffaroni | 128/260 |
| 4,327,725 | 5/1982 | Cortese et al. | 128/260 |
| 4,486,471 | 12/1984 | Samejima et al. | 427/213.3 |
| 4,503,030 | 3/1985 | Edgren et al. | 424/15 |
| 4,610,870 | 9/1986 | Jain et al. | 424/19 |
| 4,627,850 | 12/1986 | Deters et al. | 604/892 |
| 4,863,744 | 9/1989 | Urquhart et al. | 424/484 |
| 4,904,474 | 2/1990 | Theeuwes et al. | 424/424 |

(List continued on next page.)

FOREIGN PATENT DOCUMENTS

| | | |
|---|---|---|
| 28876/89 | 8/1989 | Australia . |
| 31604/89 | 10/1989 | Australia . |
| 35718/89 | 11/1989 | Australia . |
| 35747/89 | 11/1989 | Australia . |
| 40126/89 | 3/1990 | Australia . |
| 2087146 | 7/1993 | Canada . |
| 2109026 | 4/1994 | Canada . |
| 2110370 | 5/1994 | Canada . |
| 0 076 515 | 4/1983 | European Pat. Off. . |
| 0 077 956 A1 | 5/1983 | European Pat. Off. . |

(List continued on next page.)

OTHER PUBLICATIONS

English language translation of German Patent Application No. 43 18 375 A1.

Bartalsky, A., "Salicylazobenzoic Acid in Ulcerative Colitis," *Lancet* 1:960 (1982).

Brown, J. P. et al., "A Polymeric Drug for Treatment of Inflammatory Bowel Disease," *J. Med. Chem.* 26:1300–1307 (1983).

Cummings, J. H. et al., "Fermentation in the human large intestine and the available substrates," *Am. J. Clin. Nutr.* 45:1243–1255 (1987).

Cummings, J. H. et al., "Progress Report: Laxative Abuse," *Gut* 15:758–766 (1974).

Fairbairn, J. W. et al., "The Active Constituents of the Vegetable Purgatives Containing Anthracene Derivatives," *J. Pharm. Pharmacol.* 1:683–694 (1949).

(List continued on next page.)

*Primary Examiner*—Thurman K. Page
*Assistant Examiner*—William E. Benston, Jr.
*Attorney, Agent, or Firm*—Sterne, Kessler, Goldstein & FoxP.L.L.C

[57] ABSTRACT

A gastrointestinal delivery system is provided. The system comprises a drug in combination with a core material, the core being surrounded by a water-insoluble or relatively water-insoluble coating material in which particulate water-insoluble material is embedded. When the delivery device enters the gastrointestinal tract, the particulate matter takes up liquid, thus forming channels interconnecting the drug-containing core with the outside of the delivery device. These channels allow the release of drug from the core into the gastrointestinal tract. By controlling parameters in the device, such as the core material, carrier material in the coating, and particulate matter, the location of release of the drug can be carefully controlled. Thus, the invention is also directed to a method of using the device for the treatment of disease by the release of drugs in the gastrointestinal tract in a location- and time- dependent manner.

21 Claims, 8 Drawing Sheets

U.S. PATENT DOCUMENTS

| | | | |
|---|---|---|---|
| 4,983,401 | 1/1991 | Eichel et al. | 424/473 |
| 5,422,121 | 6/1995 | Lehmann et al. | 424/464 |
| 5,445,829 | 8/1995 | Paradissis et al. | 424/480 |

FOREIGN PATENT DOCUMENTS

| | | |
|---|---|---|
| 0 210 540 A1 | 2/1987 | European Pat. Off. . |
| 0 250 374 A1 | 12/1987 | European Pat. Off. . |
| 0 280 571 | 8/1988 | European Pat. Off. . |
| 0 450 176 | 10/1991 | European Pat. Off. . |
| 0 453 001 A1 | 10/1991 | European Pat. Off. . |
| 0 485 840 | 5/1992 | European Pat. Off. . |
| 0 485 840 A2 | 5/1992 | European Pat. Off. . |
| 0 551 820 A1 | 7/1993 | European Pat. Off. . |
| 0 595 110 A1 | 5/1994 | European Pat. Off. . |
| 2 306 710 | 11/1976 | France . |
| 27 17 707 | 10/1978 | Germany . |
| 43 18 375 A1 | 12/1994 | Germany . |
| 1 538 123 | 1/1979 | United Kingdom . |
| 2 174 599 | 11/1986 | United Kingdom . |
| 2 202 143 | 9/1988 | United Kingdom . |
| 89/08119 | 9/1989 | WIPO . |
| 91/07949 | 6/1991 | WIPO . |
| 92/00732 | 1/1992 | WIPO . |
| WO 92/17165 | 10/1992 | WIPO . |
| 96/04893 | 2/1996 | WIPO . |
| WO 96/04893 | 2/1996 | WIPO . |

OTHER PUBLICATIONS

Friend, D. R. et al., "Drug Glycosides: Potential Prodrugs for Colon–Specific Drug Delivery," *J. Med. Chem.* 28:51–57 (1985).

Friend, D. R. et al., "A Colon–Specific Drug–Delivery System Based on Drug Glycosides and the Glycosidases of Colonic Bacteria," *J. Med. Chem.* 27:261–266 (1984).

Gassmann, B. et al., "Pharmaceutical composition with delayed activity release," *Chemical Abstracts* 103(22), Abstract No. 183574c (1985).

Gullikson, G. W. et al., "Mechanisms of Action of Laxative Drugs," in *Pharmacology of Intestinal Permeation II*, Csaky, T. Z. (ed.), Springer–Verlag, Heidelberg, pp. 419–459 (1984).

Hardcastle, J. D. et al., "The action of sennosides and related compounds on human colon and rectum," *Gut* 11:1038–1042 (1970).

Ishino, R. et al., "Absorption of Diltiazem in Beagle Dog from Pulsatile Release Tablet," *Chem. Pharm. Bull.* 40(11):3094–3096 (1992).

Ishino, R. et al., "Design and Preparation of Pulsatile Release Tablet as a New Oral Drug Delivery System," *Chem. Pharm. Bull.* 40(11):3036–3041 (1992).

Klotz, U., "Clinical Pharmacokinetics of Sulphasalazine, Its Metabolites and Other Prodrugs of 5–Aminosalicylic Acid," *Clin. Pharmacokin.* 10:285–302 (1985).

Lancaster, C. M. et al., "Drug Delivery to the Colon: Polymer Susceptibility to Degradation by Colon Contents," *Polymer Prep.* 30:480–481 (1989).

Lehmann, K.D.R. et al., "Methacrylate–Galactomannan Coating for Colon–Specific Drug Delivery," Proceedings and Program of the 18th International Symposium on Controlled Release of Bioactive Materials, Kellaway, I.W. ed., Controlled Release Society, Inc. pub., Jul. 8–11, 1991, Amsterdam, The Netherlands.

Levine, D. S. et al., "Coating of Oral Beclomethasone Dipropionate Capsules With Cellulose Acetate Phthalate Enhances Delivery of Topically Active Antiinflammatory Drug to the Terminal Ileum," *Gastroenterology* 92:1037–1044 (1987).

Mardini, H. A. et al., "Effect of polymer coating on faecal recovery of ingested 5–amino salicylic acid in patients with ulcerative colitis," *Gut* 28:1084–1089 (1987).

Mirelman, D. et al., "Effects of Covalently Bound Silica–Nitroimidazole Drug Particles on *Entamoeba histolytica*," *J. Infect. Dis.* 159(2):303–309 (1989).

Moretó, M. et al., "3,3–Bis–(4–hydroxyphenyl)–7–methyl–2–indolinone (BHMI), the Active Metabolite of the Laxative Sulisatin," *Arzneim.–Forsch./Drug Res.* 29(II)(10):1561–1564 (1979).

Otsuka, M. et al., "Controlled Drug Release of Highly Water–Soluble Pentoxifylline from Time–Limit Disintegration–Type Wax Matrix Tablets," *Pharm. Res.* 11(3):351–354 (1994).

Rachmilewitz, D., "Coated mesalazine (5–aminosalicylic acid) versus sulphasalazine in the treatment of active ulcerative colitis: a randomised trial," *Brit. Med. J.* 298:82–86 (1989).

Rasmussen, S. N. et al., 5–Aminosalicylic Acid in a Slow–Release Preparation: Bioavailability, Plasma Level, and Excretion in Humans, *Gastroenterology* 83:1062–1070 (1982).

Rubinstein, A., "Microbially Controlled Drug Delivery to the Colon," *Biopharm. & Drug Dispos.* 11(6):465–475 (1990).

Saffran, M., "Oral insulin in diabetic dogs," *J. Endocrin.* 131(2):267–278 (1991).

Saffran, M. et al., "Oral insulin in Diabetic Dogs," *Diabetes* 38S:81A, Abstract No. 324 (1989).

Saffran, M. et al., "Vasopressin, A Model for the Study of Effects of Additives on the Oral and Rectal Administration of Peptide Drugs," *J. Pharm. Sci.* 77(1):33–38 (1988).

Saffran, M. et al., "A New Approach to the Oral Administration of Insulin and Other Peptide Drugs," *Science* 233:1081–1084 (1986).

Salyers, A. A. et al., "Cellular Location of Enzymes Involved in Chondroitin Sulfate Breakdown by *Bacteroides thetaiotaomicron*," *J. Bacteriol.* 143(2):772–780 (1980).

Salyers, A. A. et al., "Energy sources of major intestinal fermentative anaerobes," *Amer. J. Clin. Nutr.* 32:158–163 (1979).

Simpkins, J. W. et al., "Evidence for the Delivery of Narcotic Antagonists to the Colon as their Glucuronide Conjugates," *J. Pharmacol. Exper. Therap.* 244(1):195–205 (1988).

Willoughby, C. P. et al., "Distribution and metabolism in healthy volunteers of disodium azodisalicylate, a potential therapeutic agent for ulcerative colitis," *Gut* 23:1081–1087 (1982).

Supplementary European Search Report to Accompany European Application No. 91 91 0743.3, completed Aug. 11, 1993.

GASTROINTESTINAL DRUG DELIVERY SYSTEM

FIELD OF THE INVENTION

The invention is directed to a drug delivery system for delivery of enterally-administered pharmaceuticals to specific locations along the gastrointestinal tract.

BACKGROUND OF THE INVENTION

Specific delivery of drugs in pharmaceutical compositions to specific targets in the gastrointestinal tract is important in the treatment of a wide variety of diseases and conditions. Targeting drugs to specific regions along the gastrointestinal tract provides the ability to locally treat diseases, thus avoiding systemic side effects of drugs or inconvenient and painful direct delivery of drugs. Furthermore, there is an increased need for delivery of drugs absorbed at specific regions of the gastrointestinal tract. Such specific delivery would increase efficiency and enable reduction of the minimum effective dose.

There is a need for delivery to the small intestine of drugs that may be absorbed via the lymphatic system (Ritchel, W. A., *Meth Find Ex. Clin. Pharmacol* 13(5):313–336 (1991)). Macromolecules, such as peptides, could be absorbed into the lymphatics through Peyer's patches, which occur equally throughout all segments of the small intestine. Since Peyer's patches are most prevalent in young individuals and are characterized by age-related disappearance (Cornes, J., *Gut* 6:230 (1965)), they provide a target site for absorption until middle age. Targeting the Peyer's patches in a particular segment of the small intestine can be useful in limiting destructive side reactions.

The lymphatic drainage of the small intestine provides an adsorptive window and has promoted design of delivery systems directed at this window (Norimoto et al., *Int. J Pharm.* 14:149–157 (1983)).

There is also a need for delivery to the colon of drugs that are reported to be absorbable in the colon, such as steroids, xanthines, and others. This would increase the efficiency and enable reduction of the required effective dose (Godbillon, J. et al., *British Journal of Clinical Pharmacology* 19:113S (1985); Antonin, K. et al., *British Journal of Clinical Pharmacology* 19:137S (1985); Fara, J. W., *Third International Conference on Drug Absorption*, Edinburgh (1988)). Propranolol, oxyprenolol, metropolol, timolol, and benazepril are known to be preferentially absorbed in the jejunum while cimetidine, furosemide, hydrochlothiazide, and amoxicillin are known to be preferentially absorbed in the duodenum. For a review, see Rubinstein, A., *Biopharm. Drug Dispos.* 11:465–475 (1990).

Treatment of local diseases of the stomach, small intestine, and colon with topically active drugs is another incentive for site-specific delivery of drugs to the alimentary canal.

There is a need for targeting to the small intestine and colon drugs that are destroyed by the acid conditions or enzymes of the stomach. There is also a need to target to the small intestine and colon drugs that cause local irritation in the stomach.

Finally, there is a need for targeting drugs to the stomach.

However, the targeting of drugs to desired locations in the alimentary canal can be complicated.

Various factors must be taken into consideration for delivery to desirable areas of the alimentary canal. Each segment of the alimentary canal has distinct features which may hinder or favor permeation of drugs across the membrane. The following characteristics are to be taken into account:

1. Anatomic—Surface area, epithelium, presence of mucus cells, venous drainage, lymphatic drainage;
2. Physiologic features—absorption pathways, pH, motility and transit time, enzymes;
3. Biochemical features—endogenous secretion, pH, gut flora, enzymes;
4. Mechanical features—mucus and water coating layers and their turnover rate;
5. Immunological features—antigenic stimulation at the epithelial surface.

In the controlled release systems currently known in the art, drugs are released by diffusion and erosion throughout the gastrointestinal tract. Upon arrival at a target site a large portion of the drug may have already been released, leaving only a small portion of the drug for local delivery, or may pass through the site unreleased to a significant degree.

Current techniques for targeting drugs to the stomach are based on the understanding that peroral sustained-release and controlled-release may be limited in duration by gastrointestinal transit time, which is closely related to the rate of gastric emptying. Approaches for the prolongation of gastric retention time, include incorporation of fatty acids to reduce physiological gastric emptying (Groning R., et al., *Drug Dev. Ind. Pharm*, ID:527–39 (1984)) and the use of bioadhesive polymers. Such systems have been developed using polymers such as polycarbophyll, sodium carboxymethylcellulose, tragacanth gum, acrylates and methacrylates, modified celluloses and polysaccharide gums (Smart, J. D., et al., *J. Pharm. Pharmacol.* 36:295 (1984)).

Another system for targeting drugs to the stomach while avoiding gastric emptying is known as a hydrodynamically balanced system. This system is based on capsules or tablets with bulk density lower than gastric fluid. Thus, the dosage form stays buoyant in the stomach. These dosage forms are comprised of 20–75% of one or more hydrocolloids (e.g., hydroxyethylcellulose and hydroxypropylmethylcellulose (Sheth, P. R., *Drug Dev. Ind. Pharm.* 10:313–39 (1983); Chien, Y. W., *Drug Dev. Ind. Pharm* 9:1291–330 (1983); Desai, S. and Bolton, S., *Pharm. Res.* 10:1321–5 (1993)).

Banakar (*Amer. Pharm.* 27: 39–48 (1987)) describes gastroinflatable delivery devices. The devices contain one or several inflatable chambers which are filled with gas at body temperature (e.g., a gasifying liquid or a gas-forming solid, such as bicarbonate or carbonate). The chambers are incorporated within a plastic matrix and encapsulated in gelatin. Dissolution of the gelatinous coating inflates the device and drug diffusion occurs.

Certain of these devices include osmotic pressure compartments containing osmotically active salts. Dissolution of these salts by the gastric fluid pumps out the drug. Others are based upon a floating bilayer compressed matrix. (Ugani, H. M., et al., *Int. J Pharmaceut.* 35:157–64 (1987). One of the layers is comprised of a hydrophilic polymer and a carbon dioxide-generating composition. The carbon dioxide maintains buoyancy and the other hydrophilic layer releases the drug from the matrix.

A further method for gastric drug targeting involves an intragastric retention shape, made of polyethylene or polyethylene blend (Cargill, R., et al, *Pharm. Res* 5:533–536 (1988); Cargill, R., et al., *Pharm. Res.* 5:506–509 (1989)).

Mechanisms for targeting drugs to the stomach are also applied to deliver drugs to the upper small intestine. However, targeting to other areas of the small intestine involves several additional systems. The low stomach pH and presence of gastric enzymes have led to the development of enteric coating. This coating protects the gastric mucosa from drug irritation. Coating is done with a selectively insoluble substance, and protects drugs from inactivation by gastric enzymes and/or low pH.

The most common enteric coatings are methacrylic acid copolymers (Eudragits™), cellulose acetate phthalate, cellulose acetate succinate, and styrol maleic acid co-polymers (Ritschel, W. A., *Angewante Biopharmazie*, Stuttgart (1973), pp. 396–402; Agyilirah, G. A., et al., "Polymers for Enteric Coating Applications" in *Polymers for Controlled Drug Delivery*, Tarcha, P. J. ed., CRC Press, (1991) Boca Raton, pp.39–66). The most significant drawback of enteric coating is the variability in gastric emptying time. This results in a large variance in blood drug levels.

Another method of drug targeting in the small intestine is drug absorption via the lymphatic system. Capillary and lymphatic vessels are permeable to lipid-soluble compounds and low molecular weight moieties (Magersohn, M., *Modern Pharmaceutics*, Marcel Dekker, New York (1979), pp. 23–85).

Macromolecules (e.g., peptides) can be absorbed into the lymphatic system via Peyer's patches. Targeting via Peyers patches is also being considered for absorption of proteins or peptides containing antigens of tissues under autoimmune attack. At the Peyer's patches, the antigens are processed for presentation to regulatory T cells. The activated T cells migrate to the inflamed tissue, wherein suppressor cytokines neutralize T cells and any other inflammatory cells. This method is presently undergoing investigation (Ermak, T. H., et al., "Strategies for Oral Immunization and Induction of Gastric Immunity" in *Proceed. Intern. Symp. Control. Rel. Bioact. Mater.* 22:334 (1995).

The major drawback of targeting drugs/peptides to Peyers patches in their reduced availability beyond middle age (Andreasen, *Acta Patrol Microbiol. Scan.* 49 (suppl):81 (1943)).

Another approach for targeting drugs to the small intestine involves the use of intestinal sorption promoters. Studies have been carried out using long chain fatty acids, including linoleic acid, acylcarnitines, and palmitocarnitine (Morimoto, K., et. al., *Int. J Pharmaceut.* 14: 49–57 (1983); Fix, J. A., et. al., *Aires J Physiol* 14:G-332–40 (1986)).

Bioadhesives have also been used to prolong intestinal transit, as in buccal delivery systems. The adhesion to the intestinal mucosa takes place either by mechanical interlocking or other mechanisms (Longer, M. A., et. al., *Pharm. Int.* 7:114–7 (1986)).

Excipients for prolongation of GI transit time are also under development. Triethanolamine myristate has been shown to increase the gastrointestinal transit time and improve the absorption of riboflavine (Gronig, R. and Heun, G., *Drug Dev. Ind. Pharm.* 10:527–539 (1984); Palin, K. J., et al., *Int. J Pharm.*19:107–127 (1984)).

Most small intestinal-specific delivery systems are still experimental except for enteric-coated tablets. However, as discussed above, enteric coating cannot provide reproducible blood levels of drug.

Because of its location at the distal portion of the alimentary canal, the colon is particular difficult to access. Enteric coating has been used to bypass absorption in the stomach and deliver the drug to the small intestine. Delivery is based upon the pH differences between these two parts of the alimentary canal (Ritchel, W. A. *Angewndte Biopharmazio*, Stuttgart Wissensec. Verlag (1973), pp 396–402; Agyilirah, G. A. and Banker, G. S., "Polymers for Enteric Coating Applications" in *Polymers for Controlled Drug Delivery*, Tarcha, P. J., ed., CRC Press (1991) Boca Raton, pp.39–66). However, it has been demonstrated that the blood levels of enteric dosage forms are variable and erratic due to differences in gastric emptying rate. Also, enteric coatings do not allow for drug targeting to a particular part of the small intestine in a reproducible manner (Kenyon, C. J., et al., *Int. J Pharm.* 112:207–213 (1994); Ashford, M., et al. *Int. J Pharm.* 91:241–245 (1993)). Therefore, delivery systems with a different mechanism of release are necessary.

In current techniques for targeting drugs to the colon, solid formulations of the desired drug molecules are coated with a pH-resistant polymeric coating. Such formulations are similar to enteric coated formulations which may be used to deliver drugs to the distal ileum. Enteric coatings include bioerodible polymers such as shellac and cellulose acetate phthalate. (Levine et al., *Gastroenterology* 92:1037–1044 (1987)).

In contrast to the enteric coated formulations, however, the formulations for colonic delivery are designed to withstand both low and slightly basic pH values (around seven) for several hours. During this time, they are assumed to pass the stomach and the small intestine and reach the large intestine, where the coat disintegrates and the drug release process is initiated. In this way, drugs such as 5-amino salicylic acid (5-ASA), and some steroids have been delivered to the colon. The polymers used for this purpose are commonly acrylic acid derivatives or cellulose derivatives such as cellulose acetate phthalate, or ethyl cellulose (Rasmussen, S. N., et al., *Gastroenterology* 83:1062 (1982); Levine, D. S., et al., *Gastroenterology* 92:1037 (1987); Mardini H., et al., Gut 28:1084–1089 (1987)).

However, an important limitation of this technique is the uncertainty of the location and environment in which the coat starts to degrade. Depending upon the gastrointestinal motility pattern, which can vary widely in individual patients and in different disease states, degradation of the coating can occur deep in the colon, or within the small intestine.

The presence of short chain fatty acids, carbon dioxide, and other fermentation products, and residues of bile acids, often reduce the pH of the colon to approximately six (Stevens, C. E., *Amer. J. Clin. Nutr.* 31:S161 (1978); McNeil, N. I., et al, *Gut* 28:707 (1987)). This change in pH calls into question the reliance on higher colonic pH as a trigger.

U.S. Pat. No. 4,627,850 (Deters et al.) discloses an osmotic capsule for the controlled rate delivery of a drug comprising outer and inner walls each formed of a different polymeric material, the inner wall defining a space containing the drug, with a passageway through the walls connecting the exterior of the outer wall with the interior of the inner wall.

U.S. Pat. No. 4,904,474 (Theeuwes et al) discloses a colonic drug delivery device comprising means for delaying the delivery in the drug and in the small intestine and means for delivering the drug in the colon. This device comprises osmotic means for forcing the active pharmaceutical agent out from the compartment in which it is contained through an exit provided in said compartment, into the colon. The means for delaying delivery in the stomach or in the small intestine are pH-resistant coatings. The delay in delivery of the drug is time-based. The structure is so calculated that the contents of the inner drug-filled space are not forced out before the device has reached the preselected target region of the gastro-intestinal tract.

The ability of the colonic flora to degrade substrates that are resistant to small bowel digestion has been studied as an alternative method for colonic delivery of drugs. This principle was utilized to deliver laxative products, mainly sennoside and related compounds (Fairbairn, J. W., *J. Pharm. Pharmacol.* 1:683 (1949); Hardcastle, J. D., et al., *Gut* 11:1038 (1970); Cummings, J. H., *Gut* 15:758 (1974)).

A drug traditionally used in the treatment of inflammatory bowel disease is sulfasalazine. Sulfasalazine is composed of the antibacterial sulfapyridine linked to the anti-inflammatory 5-ASA with an azo bond. The 5-ASA is responsible for the clinical effect (Khan, A. K., et al., *Lancet* 2:892 (1977)). The sulfasalazine is a prodrug which carries the active 5-ASA to the colon, where bacterial azo reduction releases the molecule with the desired therapeutic properties (Klotz, U., *Clin. Pharmacokin.* 10:285 (1985)).

With the 5-ASA pro drugs (sulfasalazine, azodisalicylate and salicylazo-benzoic acid), release of the parent drug is mediated by bacterial enzymes located at the target organ, rather than by enzymes of the target tissues. The realization that enzymes characteristic of inhabitant microorganisms of the colon may convert prodrugs and other molecules to active therapeutics led to an increase in research activity in the area of microbially controlled drug delivery to the colon.

While there is evidence that certain proteins and peptides such as interleukin-II, interferon, colony-stimulating factor, tumor necrosis factor, and melanocyte-stimulating hormone may create new and effective therapies for diseases that are now poorly controlled, the acceptance of these proteins as drugs is currently limited by the methods of delivery. Colonic delivery may be a preferred route of administration for these and other new protein and peptide drugs.

Colonic delivery is also important for targeting drugs for the treatment of inflammatory bowel disease and ulcerative colitis. However, the currently available enterally administered preparations of drugs designed for colonic delivery are not feasible for long-term use in humans, in part because of the potential toxicity of the azo compounds. There exists a need for an improved colonic delivery system that can be used with a wide variety of drugs and bioactive compounds.

In copending application Ser. Nos. 08/193,775 and 08/481,148, filed on Feb. 10, 1994 and Jun. 7, 1995, respectively, a delivery device is disclosed comprising a drug in combination with a matrix, the matrix comprising a saccharide-containing polymer. The matrix-drug combination can be coated or uncoated. The polymer can be resistant to chemical and enzymatic degradation in the stomach and susceptible to enzymatic degradation in the colon by colonic bacteria. Whether the matrix is resistant or not to chemical and enzymatic degradation in the stomach, the mechanism of release of drug in the colon is by degradation of the matrix by colonic bacteria and the release of the drug embedded in the matrix as a result of the degradation of the matrix by colonic bacterial enzymes. The disclosure of this copending application is incorporated herein by reference in its entirety for its teaching and guidance regarding the use and preparation of colonic delivery devices.

European patent 485840 (to Röhm GmbH), the application for which was published May 20, 1992, discloses a gastrointestinal delivery device containing, as a coating, a mixture of a polysaccharide and Eudragit™. However, this formulation allows the rapid entry of liquid and the rapid exit of drug such that controlled release of the drug cannot be achieved as with the present invention. Further, the polysaccharide is not provided in particulate form.

According to the present invention, however, these problems are overcome because the coating used for the invention prevents drug release until the predetermined time when particulates in the coating have swollen enough to allow for drug release.

SUMMARY OF THE INVENTION

The invention is directed to a delivery system or device for targeted delivery to specific locations in the alimentary canal comprising a core and a coating. The core is comprised of a drug in combination with a carrier material. In preferred embodiments, this carrier material has the property of swelling upon contact with an aqueous medium such as that found in the alimentary canal.

The form of the core includes tablets, capsules, and pellets, especially compressed tablets and matrix tablets.

The coating comprises a material that is not soluble, or minimally soluble, in aqueous solution, within which material a hydrophilic, non-water-soluble, particulate is imbedded.

This design allows the slow introduction of water or aqueous fluid, such as in the gastrointestinal tract, into the device. When the water reaches the particulate matter, the particulate matter swells. The particles eventually form channels from the outer part of the device to the core containing the drug. The drug can then be released from the channels. In embodiments in which the core is swellable, the core then swells and the drug is released in a controlled manner through the channels formed from the embedded particulate.

For non water-soluble drugs, it is preferable that the core be swellable. For water-soluble drugs, it is preferable that the core be non-swellable. Of course, depending on the drug, the core may be designed with varying degrees of swellability.

The location of drug release is controlled by varying specific parameters such as the thickness of the outer coating, the amount of particulate embedded in the coating, the type of particulate embedded in the coating, the particle size distribution of the particulate embedded in the coating and the core carrier. Thus, the drug delivery system of the invention further provides a method for enterally administering a drug or other bioactive compound to a patient in need of such drug whenever it is necessary that such drug should be specifically provided locally in the gastrointestinal tract.

The preferable areas of treatment include, but are not limited to, the ileum and the colon.

The drug delivery system further provides a method for delivering efficacious levels of one or more drugs designed for local treatment of diseases of particular areas of the alimentary tract. These diseases include, but are not limited to, Crohn's disease, colitis, irritable bowel syndrome (IBS), local spasmolytic action, ulceration of the mucosa, diarrhea, constipation, polyps, carcinomas, cysts, infectious disorders, and parasitic disorders. The drug delivery system further provides a method for oral immunization through either the Peyer's Patches or through the colon (Cardenas, L. and Clements, J. D., *Clin. Microbiol Rev.* 5/3: 328–342 (1992)). The drug delivery system further offers the opportunity for targeting the local delivery of agents for photodynamic therapy.

The drug delivery system also provides a method for the systemic delivery of efficacious levels of drugs through a targeted area of the alimentary canal. Drugs that are better absorbed, and/or show lesser side effects, in the distal parts of the alimentary canal can be directed to those sites. The delivery system allows delivery to the duodenum, jejunum, ileum, ascending colon, transverse colon, and descending colon as the site for systemic drug delivery.

The invention further provides methods for the preparation of the drug delivery system. The preferred method of preparation is by the preparation of a suspension of the hydrophilic, water-insoluble particulate in an alcoholic solution of a hydrophobic polymer. This suspension is spray coated onto the core tablet or capsule using conventional pan coating technology.

DETAILED DESCRIPTION OF THE PREFERRED EMBODIMENTS

Definitions

Figure 1:
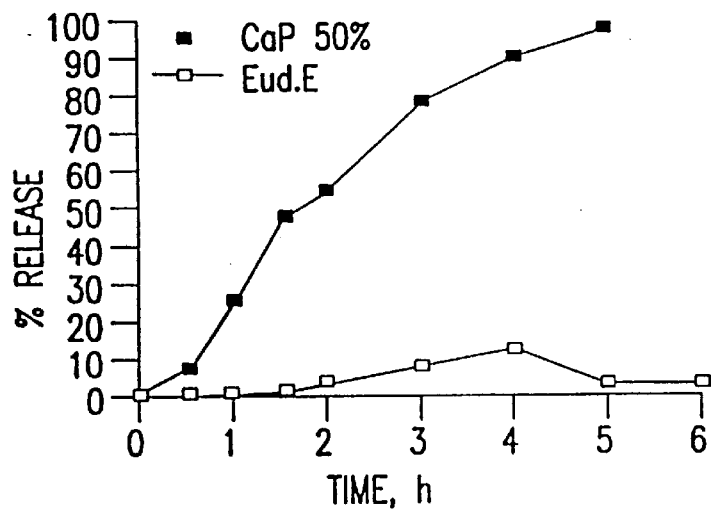
FIG. 1. Sodium salicylate diffusion through 200μ Eudragit E™ and Eudragit E™/calcium pectinate (1:1) films.

In the description that follows, a number of terms used in pharmacology are extensively utilized in order to provide a clear and consistent understanding of the specification and claims, and the scope to be given such terms, the following definitions are provided. Where not specifically indicated, the terms used herein are used according to their normal and/or art-recognized meaning.

For example, the terms "colon", "large intestine", "small intestine", "stomach", "rectum" and "ileum" are all used according to their art-recognized meanings.

By the term "drug" is meant any pharmaceutical or physiological agent, composition, bioactive compound, or combination thereof, useful in the diagnosis, cure, mitigation, treatment, or prevention of a disease, or for any other medical purpose. The term "drug" is intended to be interpreted broadly and is not limited in terms of chemical composition or biological activity.

A "core", the central part of anything, with respect to the present invention, relates to that part of the drug delivery system that is surrounded by the particulate-containing coating and which contains the drug to be released from the delivery system. The drug may be embedded in the core or otherwise associated with it, for example by dry admixture, or wet granulation. The core may be a matrix tablet or a capsule containing the drug or pellets of the pure drug or pellets of the drug layered on a core material or microcapsules containing the drug material. In all of these, release of drug from the core is effective.

The core material includes, but is not limited to combinations of pectin, calcium pectinate, microcrystalline starch, hydroxypropylmethylcellulose, lactose, starch, polyvinylpyrrolidone, microcrystalline cellulose, calcium phosphate, guar gum, and normal pharmaceutical additives and excipients. (See *Handbook of pharmaceutical Excipients,* 2nd ed., Wade, A. and Weller, P. J., eds., American Pharmaceutical Association (1994)).

In preferred embodiments, the core material comprises calcium pectinate, hydroxypropylmethylcellulose, microcrystalline cellulose, starch, or microcrystalline starch or any combination thereof. Alternate core materials include, but are not limited to, carboxymethylcellulose, lactose, polyvinylpyrrolidone, guar gum, alginic acid, sodium alginate, carrageenan, or any standard tablet excipient known to those in the art. (See *Handbook of Pharmaceutical Excipients,* 2nd ed., Wade, A. and Weller, P. J., eds., American Pharmaceutical Association (1994)).

The term "particulate" refers to a composition composed of separate particles. In the context of the present invention, these separate particles are embedded in the coating material surrounding the core. It is the taking up of liquid by these particles that creates channels, pores, or networks that allow the release of drug from the core to the outside of the device. Drug release can be through such channels.

In the context of the invention, "coat", "coating", "film", "layer", "covering", and the like are interchangeable.

The particulate matter includes, but is not limited to, polysaccharides. Such polysaccharides include, but are not limited to calcium pectinate, calcium alginate, calcium xanthate, any metal salt of a polysaccharide containing an acid group where the salt renders the polysaccharide insoluble in water, microcrystalline starch, insoluble starch, any water insoluble polysaccharide (e.g. cellulose or microcrystalline cellulose), any polysaccharide rendered insoluble by interacting with a poly-cation or poly-anion, and any covalently crosslinked polysaccharide where said crosslinking renders the polysaccharide insoluble in water. Such crosslinking agents include, but are not limited to, glutaraldehyde, formaldehyde, epichlorohydrin, diacid chlorides, diisocyananates, diacid anhydrides, and diamines.

The coating material may optionally contain a plasticizer to improve its properties as is known in the art. The coating may be optionally coated with an outer coating of a normal enteric coating, as known in the art, if the coating material or the particulate is affected by the acid conditions of the stomach.

Further outer coatings include, but are not limited to, coatings to ease swallowing or mask taste.

In preferred embodiments, the coating material comprises calcium pectinate and Eudragit E™, Crospovidone and Eudragit E™, or calcium pectinate and ethylcellulose. In this embodiment the particulate matter comprises calcium pectinate or Crospovidone while the Eudragit E™ or ethylcellulose comprises the water insoluble carrier.

The water insoluble carrier may or may not include a plasticizer according to the normal properties of a film as known to those skilled in the art.

In alternate embodiments, the coating includes, but is not limited to, any combination of a water-insoluble polysaccharide, water-insoluble crosslinked polysaccharide, a water-insoluble polysaccharide metal salt, a water-insoluble crosslinked protein or peptide, a water-insoluble crosslinked hydrophilic polymer in a dried powder form as the particulate and any hydrophobic polymer coating known in the art as the water-insoluble carrier. Specific examples of the particulate material include, but are not limited to, insoluble starch, microcrystalline starch, microcrystalline cellulose, chitosan, calcium or zinc alginate, calcium xanthate, guar gum borax complex, glutaraldehyde- or formaldehyde-crosslinked guar gum, glutaraldehyde- or formaldehyde-crosslinked dextran, epichlorohydrin-crosslinked dextran, glutaraldehyde- or formaldehyde-crosslinked soluble starch, glutaraldehyde-or formaldehyde-crosslinked hydrolyzed gelatin, glutaraldehyde- or formaldehyde-crosslinked gelatin, glutaraldehyde- or formaldehyde-crosslinked collagen, any insoluble complex of a polysaccharide and a protein or peptide, glutaraldehyde- or formaldehyde-crosslinked hydroxypropylcellulose, glutaraldehyde- or formaldehyde-crosslinked hydroxyethylcellulose, glutaraldehyde- or formaldehyde-crosslinked hydroxypropylmethylcellulose, or any of the carbomers (crosslinked acrylic acid polymers). Specific examples of the water-insoluble carrier include, but are not limited to, Eudragit E™, Eudragit NE™, Eudragit RL™, Eudragit RS™, ethylcellulose, shellac, zein, and waxes.

The term "water-insoluble" means not susceptible to being dissolved. Within the context of the present invention, the property of water-insolubility is important as follows. Both the hydrophobic film and the hydrophilic particulate are water-insoluble and insoluble in the fluids of the intestine. This property is important for the hydrophobic film so as to prevent the premature dissolution of the film coat and the subsequent non-controlled release of the drug. The property is furthermore important for the hydrophilic particulate so that the channels formed remain intact and continue to control the release of the drug. The dissolution of the particulate would result in empty channels that would cause undesirable accelerated drug release.

Conversely, the term "water-soluble" means susceptible of being dissolved. The term "hydrophobic" when applied to a film means, besides its normal definition, relatively non-permeable to water and to water-soluble compounds. The term "hydrophilic", when applied to a film, means, besides its normal definition, relatively permeable to water and to water-soluble compounds.

The term "embedded" or "embed" means the firm fixation of a material in a medium. Within the context of the present invention, this term refers to particulate matter fixed in the coating medium.

The term "microcapsule", "microparticle", and "microsphere" are used in the art-recognized sense as spheroidal or partly spheroidal particles in the submicron to approximate 1000 micron range. The preferred ranges are from 1 to 200 microns, and especially from 2 to 100 microns.

The term "channel" means that through which anything flows. In the context of the present invention, it is the connection formed from the uptake of water and swelling of the particulate matter in the coating such that there is continuous contact among the swollen particulate matter to form conduits through which the aqueous medium outside of the delivery device is ultimately brought into contact with the core material in the device.

The term "administer" is intended to mean introducing the device of the present invention into a subject. When administration is for the purpose of treatment, administration may be for either prophylactic or therapeutic purposes. When provided prophylactically, the substance is provided in advance of any symptom. The prophylactic administration of the substance serves to prevent or attenuate any subsequent symptom. When provided therapeutically, the substance is provided at (or shortly after) the onset of a symptom. The therapeutic administration of this substance serves to attenuate any actual symptom.

The term "animal" is intended to mean any living creature that contains cells in which the devices of the present invention can be effective. Foremost among such animals are humans; however, the invention is not intended to be so limiting, it being within the contemplation of the present invention to apply the compositions of the invention to any and all animals which may experience the benefits of the invention. Thus, the delivery system and methods of the invention not limited to administration to humans and are especially useful for veterinary administration of drugs to any animal, including (but not limited to) pets such as dogs, cats, horses, fish and birds, zoo animals, wild animal control and treatment, and agriculturally important animals of the food and dairy industry such as cattle, milk cows, swine and poultry.

The invention is directed to a device containing a water-insoluble or relatively water-insoluble coating around a drug-containing core and especially a swellable core. The coating is a mixture of a water-insoluble hydrophilic particulate material embedded and dispersed in a non-watersoluble material. The coating may not be completely non-water-soluble. However, the important parameter is that it allows the slow introduction of water or other aqueous fluid, such as in the gastrointestinal tract. When the water reaches the embedded hydrophilic particles, they swell. The swelled particles eventually form channels from the outer part of the device to the core containing the drug. The drug is released through these channels in a controlled manner. In embodiments in which the core is swellable, the core then swells and drug is released in a controlled manner through the channels formed from the embedded particulate.

In a preferred embodiment of the invention, the delivery device is a tablet that contains a core material which is a naturally non-disintegrating tablet. The tablet is made with standard granulation and tableting techniques and is coated using pan coat technology. Instead of a solution, a suspension of the particulate material in a solution or fine suspension of the polymeric coating material is sprayed on the tablets. The suspension is stirred to keep it relatively homogeneous. Warm or cold air is flowed over the tablets to allow for the film to form and the tablets to dry. Suitable solvents for such polymeric solutions or suspensions are the typical solvents known to those in the art for spray coating tablets and include, but are not limited to, water, ethanol, acetone and isopropanol. Ethanol is the preferred solvent.

In a further preferred embodiment of the invention, the device is in the form of a coated tablet. Alternate forms of the device are coated capsules, coated microcapsules, coated pellets or micropellets, coated pellets or micropellets in a capsule, coated pellets or micropellets in a coated capsule, coated pellets, micropellets or microcapsules pressed into a tablet and coated pellets, micropellets or microcapsules pressed into a tablet and further coated.

It should be recognized however that any material, and any swellable material, is potentially useful as the core material. The functional requirement is simply that upon contact with aqueous matter in the gastrointestinal tract and following contact with channels formed by the particulate matter that has absorbed water, the core allows the drug present in the core to be released.

This may be through the channels of the release device. In embodiments in which a swellable core in desired, any material may be used as empirically determined to cause the necessary amount of swelling.

It should also be recognized that any material can form the embedded particulate. The functional requirement is that the material absorb aqueous matter from the gastrointestinal tract thereafter forming channels or networks whereby aqueous matter can flow and drug can be released.

Drug release is controlled by varying the following parameters: (1) size of the particulate matter; (2) thickness of the coating; (3) type of material forming the particulate matter; (4) ratio of particulate matter; and (5) water-insoluble film forming material.

In particularly preferred embodiments, the device is a 9 mm tablet of a drug (e.g., sodium salicylate or sodium diclofenac) and excipients (e.g., calcium pectinate, pectin, and hydroxypropylmethylcellulose) coated with a suspension of 7 parts calcium pectinate and 3 parts Eudragit™ E in 25 to 30 parts ethanol. The best results are obtained with calcium pectinate of particle size <149$\mu$ and a film thickness of approximately 200 microns. This embodiment allows for delivery of a soluble drug to the colon since it affords an approximate four hour delay in drug release under in vitro conditions of USP Intestinal TS (*U.S. Pharmacopeia XXII, National Formulary XVII*, page 1789 (1990)) when using dissolution apparatus 2 (*U.S. Pharmacopeia XXII, National Formulary XVII*, page 1579 (1990)).

The preferred embodiment is coated with Eudragit L™ as an enteric coat to protect both the Eudragit E™ and the calcium pectinate from the effects of the acid pH of the stomach. The enteric coat dissolves in the upper part of the small intestine. The particulate calcium pectinate starts to slowly swell as intestinal fluid enters the coating. After about four hours, channels have formed and the soluble drug starts to release from the system. The soluble drug load of this system is released in a controlled fashion by diffusion through the channels of swollen calcium pectinate after reaching the colon. A thinner coat will reduce the delay in drug release and allow delivery of the drug to the distal portion of the small intestine.

For colonic administration, the formulation is designed so as to prevent release of the drug in the stomach and small intestine environments and to be unaffected by the stomach and small intestine enzymes. When targeting the colon, the preferred embodiment has the advantage of the guaranteed release of the drug load since the major portion of the coating system (70% calcium pectinate) and the core (calcium pectinate and pectin) are enzymatically degradable in the colon while being non-degradable by enzymes of the stomach and small intestine.

The formulation will thus permit release of the drug, by diffusion through the swollen channels of the particulates, upon arrival in the colon as well as by the action of colonic bacteria. The bacteria will degrade the particulate material further opening the channels. The bacteria will then enter the core by the opened channels formed, degrade the core material, and thus facilitate colonic drug release.

Thus, the drug delivery system serves as a means to target enterally administered drugs to various regions of the gastrointestinal tract. Accordingly, a subject in need of treatment with the desired agent, may conveniently obtain such treatment by orally ingesting the compositions of the invention.

Examples of agents that are useful for colonic delivery include nonsteroidal anti-inflammatory drugs (NSAID) such as diclofenac, flurbiprofen, indomethacin, and aspirin; steroid drugs such as dexamethasone, budesonide, beclomethasone, flucticasone, tioxocortol, and hydrocortisone; contraceptives or steroidal hormones such as estrogen, estradiol and testosterone; immunosuppressants such as cyclosporin; bronchodialators such as theophylline and salbutamol; anti-anginals and anti-hypertensives such as isosorbide dinitrate, isosorbide mononitrate, nitroglycerine, nifedipine, oxyprenolol, diltiazem, captopril, atenolol, benazepril, metoprolol, and vasopril; anti-spasmodic agents such as cimetropium bromide; anti-colitis agents such as 5-aminosalicylic acid; anti-arrhythmia agents such as quinidine, veraparnil, procainamide, and lidocaine; anti-neoplastic agents such as methotrexate, tamoxifen, cyclophosphamide, mercaptopurine, and etoposide; protein or peptide drugs such as insulin, human growth hormone, interleukin-II, interferon, calcitonin, leuprolide, tumor necrosis factor, bone growth factor, melanocyte-stimulating hormone, captopril, somatostatin, somatostatin octapeptide analog, cyclosporin, renin inhibitor, superoxide dismutase, other hormones and vaccines; anticoagulants such as heparin or short chain heparin, anti-migraine drugs such as ergotomine; glibenclamide; 5-hydroxytryptamine type$_{1A}$ receptor agonist gepiron; 5HT$_3$ antagonist ondasteron; metkephamid; menthol; antibiotics such as neomycin, β-lactams such as ampicillin and amoxicillin, cephalosporins such as cephalexin and cloxacillin, and macrolides such as erythromycin; and $PGE_1$ analogues for protecting the gastroduodenal mucosa from NSAID injury, such as misoprostol. Protein drugs, such as LH-RH and insulin, may survive longer and be absorbed better from the colon than from the small intestine. Other drugs have been shown to possess colonic absorption, such as diclofenac, quinidine, theophylline, isosorbide dinitrate, nifedipine, oxprenolol, metoprolol, glibenclamide, 5-hydroxytryptamine type$_{1A}$ receptor agonist gepiron, $5HT_3$ antagonist ondasteron, metkephamid, menthol, benazepril (ACE inhibitor).

Examples of drugs that are useful for treating various other regions of the alimentary canal are as follows: Gastro Esophagal Reflux Disease—H2 receptor antagonists (e.g., Tagamet, Zantac), proton pump inhibitors (e.g., Omeprazole); Candida esophagitis—nystatin or clotrimazole; Duodenal Ulcer—H2 receptor agonists, prostaglandins (e.g., Cytotec, Prostin), proton pump inhibitors—(e.g., Prilosec, Omeprazole, Sucralfate); Pathological Hypersecretory Conditions, Zollinger-Ellison Syndrome—H2 receptor agonists; Gastritis—H2 receptor agonists, $PGE_1$ analogs for protecting the gastroduodenal mucosa from NSAID injury such as misoprostol, GHR-IH drugs for treating pancreatitis, such as somatostatin, and anti-spasmodic drugs for treating local spasmolytic action such as cimetropium bromide.

The therapeutic benefits of the delivery system depend upon its ability to delivery efficacious levels of drugs to a specific site in the gastrointestinal tract. This allows the local treatment of diseases including, but not limited to, ulcerative colitis, Crohn's disease, colon carcinoma, esophagitis, Candida esophagitis, duodenal ulcers, gastric ulcers, Zollinger-Ellison Syndrome (gastrinoma), gastritis, chronic constipation, pancreatitis, local spasms, local infections, parasites, and other changes within the gastrointestinal tract due to effects of systemic disorders (e.g., vascular inflammatory, infectious and neoplastic conditions).

Direct delivery of drugs to these regions enhances the amount of drug absorbed in this region and the amount of drug to which the cells in the region are directly exposed. Direct delivery or targeting of drugs also decreases the systemic distribution of drugs and thereby reduces undesirable and potentially harmful side effects.

The devices are also useful for diagnostic purposes, such as site-specific delivery of x-ray contrast agents (e.g., barium sulfate, Diatrizoate Sodium, other iodine containing contrast agents) ultrasound contrast agents (e.g., air-containing microspheres), contrast or enhancement agents for Magnetic Resonance Imaging, Tomography, or Positron Emission agents. The devices are further useful for the delivery of monoclonal antibody markers for tumors.

Specific embodiments of prepared formulations of the compositions of the invention, include, for example, matrix-drug tablets, especially tablets prepared by compression; matrix-drug pellets, either free or packed in gelatine capsules, or any other means allowing oral administration; matrix-drug nanoparticles, either free or packed in gelatine capsules or any other means allowing oral administration; and multi-layered tablets, coated capsules, coated microcapsules, coated pellets or micropellets, coated pellets or micropellets in a capsule, coated pellets or micropellets in a coated capsule, coated pellets, micropellets or microcapsules pressed into a tablet and coated pellets, micropellets or microcapsules pressed into a tablet and further coated. All of the techniques for preparation of such formulations are well known in the art.

The amount of drug can vary as desired for efficacious delivery of the desired drug and in consideration of the patient's age, sex, physical condition, disease, and other medical criteria. In addition, the amount of drug delivered by the system of the invention will depend upon the relative efficacy of the drug. The amount of specific drug necessary for efficacious results in the delivery system and methods of the invention may be determined according to techniques known in the art. For example, recommended dosages such as known in the art (for example, see the *Physicians' Desk Reference,* (E. R. Barnhart, publisher), *The Merck Index,* Merck & Co., New Jersey, and *The Pharmacological Basis of Therapeutics,* A. G. Goodman et al, eds., Pergamon Press, New York), provide a basis upon which to estimate the amount of a drug which has been previously been required to provide an efficacious level of activity.

Examples of drugs whose efficacious amounts for use in the delivery system of the invention may be determined in this manner include anti-inflammatory agents, including non-steroidal and steroidal anti-inflammatory agents, such as indomethacin, diclofenac, flurbiprofen, aspirin, dexamethasone, budesonide, beclomethasone, flucticasone, tioxocortal, and hydrocortisone; immunosuppressants, such as cyclosporin; bronchodialators, such as salbutamol and theophylline; anti-anginals and anti-hypertensives, such as diltiazem, captopril, nifedipine, isosorbide dinitrate, oxyprenolol; anti-spasmodics, such as cimetropium bromide; anti-neoplastic agents, including methotrexate, tamoxifen, cyclophosphamide, mercaptopurine etoposide; anti-colitis drugs, such as 5-aminosalicylic; and anti-arrhythmia agents, such as quinidine, verapamil, procainamide and lidocaine; protein or peptide drugs, such as insulin, human growth hormone, interleukin-II, interferon, calcitonin, leuprolide, tumor necrosis factor, bone growth factor, melanocyte-stimulating hormone, captopril, somatostatin, somatostatin octapeptide analog, cyclosporin, renin inhibitor, superoxide dismutase; other hormones; vaccines; anti-coagulants, such as heparin or short chain heparin; and anti-migraine drugs, such as ergotamine.

Tablets and capsules may be prepared and tested by techniques well known in the art, for example, as described in *Remington's Pharmaceutical Sciences,* Mack Publishing Company, and especially in chapter 89, the pharmaceutical preparation and manufacture of "Tablets, Capsules and Pills." In all embodiments, if desired, more than one drug may be supplied to the patient in the same matrix.

In the tablet embodiments, for example, the compositions of the invention may provide a wide range of drug amounts, for example, the amount of drug can vary from about 0.01–95% by weight.

In another embodiment, a compressed tablet is formulated to contain efficacious levels of the desired drug(s) or pharmaceutical compound(s) as in the tablet embodiment, and an amount of the components of the invention that would allow disintegration of the tablet and release of the drug(s) following exposure of the tablet to one or more microorganisms present in the colon. Other suitable embodiments will be known to those of skill in the art.

The following examples further describe the materials and methods used in carrying out the invention. The examples are not intended to limit the invention in any manner.

EXAMPLE 1

Materials and Methods

Eudragit E™ 100 and Eudragit RS™ were purchased from Rohm Pharma (Germany). Ethyl Cellulose was purchased from Hercules (USA). Sodium salicylate powder (BP, USP) was supplied by Merck (Germany). Sodium diclofenac was purchased from Prosintex (UK). Ethyl alcohol was USP grade. Calcium pectinate powder containing 4% and 2% calcium was prepared by the addition of calcium chloride to a suspension of low methoxy pectin (Copenhagen Pectin) in a water/isopropyl alcohol mixture. Pectin/calcium pectinate core tablets which weighed ~300 mg and contained 30 mg sodium salicylate were prepared by standard dry granulation techniques. Microcrystalline cellulose core tablets weighing 250 mg and containing 30 mg sodium salicylate, were prepared by dry granulation techniques. Pectin/calcium pectinate core tablets weighing ~300 mg and containing 100 mg sodium diclofenac were prepared by standard dry granulation techniques. Crospovidone was purchased from GAF (USA). Crosslinked Byco gelatin was prepared by a crosslinking reaction of Byco hydrolyzed gelatin (Croda (UK)) with glutaraldehyde (Merck (Germany)). Microcrystalline cellulose was purchased from FMC (Belgium). The coating calcium pectinate/Eudragit™ suspension was prepared by dissolving Eudragit E™ (10% w/v (22.5 g Eudragit™/200 g solution)) in ethanol and then adding the calcium pectinate powder, to the desired weight ratio of, 70, 50 and 30% (g calcium pectinate/g Eudragit™ plus calcium pectinate), to the Eudragit™ solution. The suspension was then continuously stirred vigorously throughout the coating process to prevent the calcium pectinate deposition. The other polymer—particulate combinations were prepared similarly by first dissolving the polymer (Eudragit RS™ or ethylcellulose) in ethanol and then adding the particulate (calcium pectinate, Crospovidone, microcrystalline cellulose, or crosslinked Byco protein).

Figure 23:
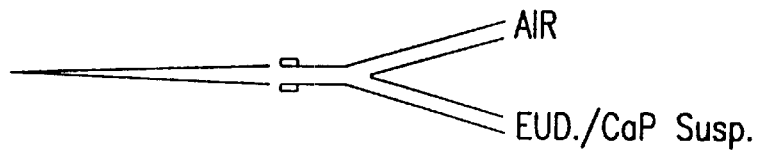
FIG. 23. Schematic of spray coating nozzle device referred to in Example 1 herein.

Spray coating was performed on 100 g tablets (Pectin/calcium pectinate tablets or mixtures of Pectin/calcium pectinate tablets with microcrystalline cellulose tablets). The coating system consisted of a pan coater (~12 cm diameter), an Erweka or Heidolph (RZR 2051, electronic) driving motor, a peristaltic pump (Masterflex, Digital Console Drive, Cole-Palmer Instrument Company) and a nozzle composed from a "Y" tube and a pipette tip, as illustrated below in FIG. 23.

The peristaltic pump provided a constant flow of the suspension (3 ml/min.) using #16 type silicon tubing. The pressure of the air used for spraying was in the range of 5–10 psi. Sampling and coating thickness measurements of both microcrystalline cellulose and calcium pectinate/pectin tablets was carried out after spraying of 50 ml suspension and at 50 ml intervals up to 250 ml. Dissolution studies were carried out in intestinal fluid TS using a Vankel VK 7000 dissolution tester. Each tablet was placed in 900 ml intestinal fluid TS and stirred by paddle at 50 RPM. Intestinal fluid TS was prepared according to USP XXII p. 1789 (without pancreatin). The solutions were kept at 37° C. by a Vankel VK650A heater/circulator. Samples (3 ml) were taken at various time intervals as indicated by the time points in each experiment using a Vankel VK8000 Autosampler. The sodium salicylate released from the coated tablets was quantified using a HP 8452A Diode-Array Spectrophotometer at 296 nm. Experiments carried out with sodium diclofenac were quantified using a wavelength of 276 nm.

The measurement of the diffusion of sodium salicylate through free-standing sprayed films was carried out on 200μ thick sprayed Eudragit E™/calcium pectinate and Eudragit E™ films using a diffusion cell. The area of the film available for diffusion was 2.27 cm².

Intestinal TS solution (9 ml) was placed in the receiver cell and 100 ppm of sodium salicylate dissolved in intestinal TS was placed on the other side of the film. The films were pre-wetted in water/ethanol mixture (4/1 v/v) for 5 minutes. The entire assembly was placed in a shaker bath held at 37° C. and shaken at 70 strokes per minute. Samples of 1 ml were taken by syringe at predetermined time intervals, measured for sodium salicylate content by UV spectroscopy at 296 nm, and returned to the cell.

The Eudragits™ are disclosed in the Röhm Pharma Technical material. They are characterized as (1) an anionic copolymer based on methacrylic acid and methylmethacrylate wherein the ratio of free carboxyl groups to the ester groups is approximately 1:1, (2) an anionic copolymer based on methacrylic acid and methylmethacrylate wherein the ratio of free carboxyl groups to the ester groups is approximately 1:2, (3) a copolymer based on acrylic and methacrylic acid esters with a low content of quaternary ammonium groups wherein the molar ratio of the ammonium groups to the remaining neutral methacrylic acid esters is 1:20, and (4) a copolymer based on acrylic and methacrylic acid esters with a low content of quaternary ammonium groups wherein the molar ratio of the ammonium groups to the remaining neutral methacrylic acid esters is 1:40, said copolymers being sold under the trademarks "Eudragit L," "Eudragit S," "Eudragit RL," and "Eudragit RS," respectively. Emcocel and Avicel are trademarks for microcrystalline cellulose. Eudragit E™ is a cationic copolymer based on diethylaminoethyl methacrylate and neutral methacrylic acid esters. Eudragit NE™ is a neutral copolymer based on poly(meth)acrylates. Both are discussed in Röhm Pharma commercial literature.

RESULTS

Diffusion of Sodium Salicylate (SS) Through Free Films

The results of the diffusion of sodium salicylate through free films of Eudragit E™ and Eudragit E™/calcium pectinate (1:1) are shown in FIG. 1. The films were 200μ thick in both cases. Essentially no diffusion of drug occurred through the Eudragit E™ film throughout the experiment. The Eudragit E™/calcium pectinate film allowed the movement of sodium salicylate at a controlled rate. 50% of the sodium salicylate had diffused through the film in two hours. The diffusion was essentially complete in five hours.

Effect of Calcium Pectinate Content on the Diffusion of Sodium Salicylate from Tablets Tablets of 30 mg sodium salicylate (chosen as a very soluble drug marker) in a calcium pectinate/pectin matrix were coated with various thicknesses of the Eudragit E™/calcium pectinate film coating at various ratios of calcium pectinate to Eudragit E™. The results are summarized in FIGS. 2–5.

Figure 2:
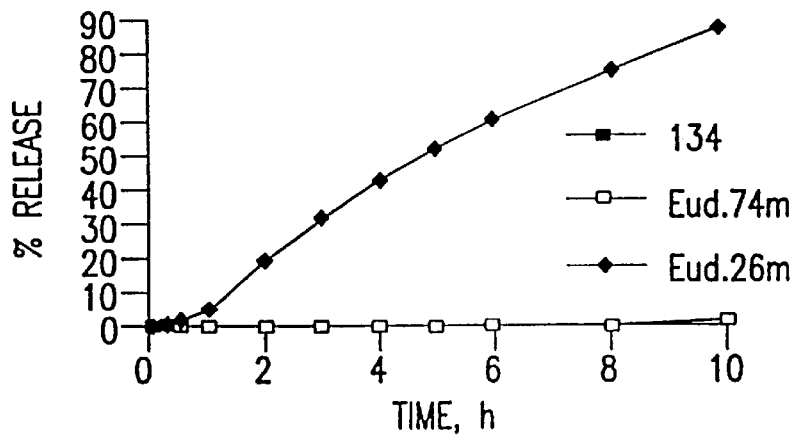
FIG. 2. Sodium salicylate release from calcium pectinate/pectin cores coated with Eudragit E™.

FIG. 2 shows the release of sodium salicylate from tablets coated with Eudragit E™ only. Tablets coated with a film of 74μ or more of Eudragit E™ were impenetrable for ten hours. Tablets coated with a thin coat of Eudragit E™ allowed diffusion of the sodium salicylate after a short lag time. After the lag time, the profile was similar to that of a non-coated tablet.

Figure 3:
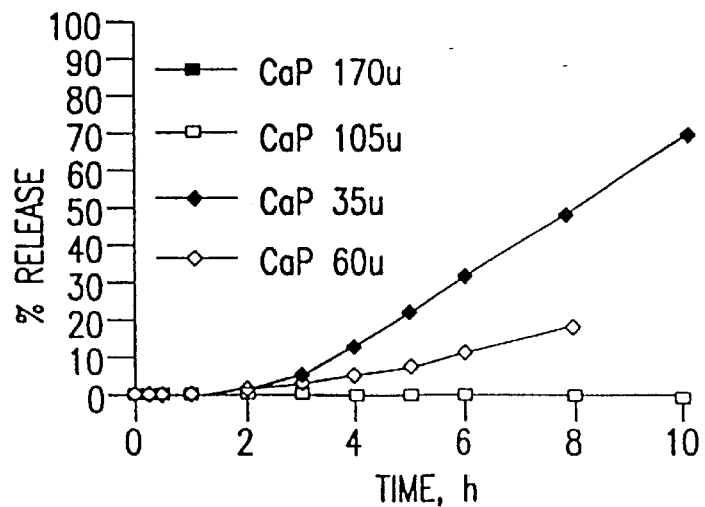
FIG. 3. Sodium salicylate release from calcium pectinate/pectin cores coated with Eudragit E™/calcium pectinate (7:3) films.

FIG. 3 shows sodium salicylate release from tablets coated with Eudragit E™/calcium pectinate (7:3). Tablets coated with a coating thicker than 105μ were impenetrable to drug diffusion. A 60μ coating allowed slow drug diffusion. Approximately 10% diffused out after six hours.

Figure 4:
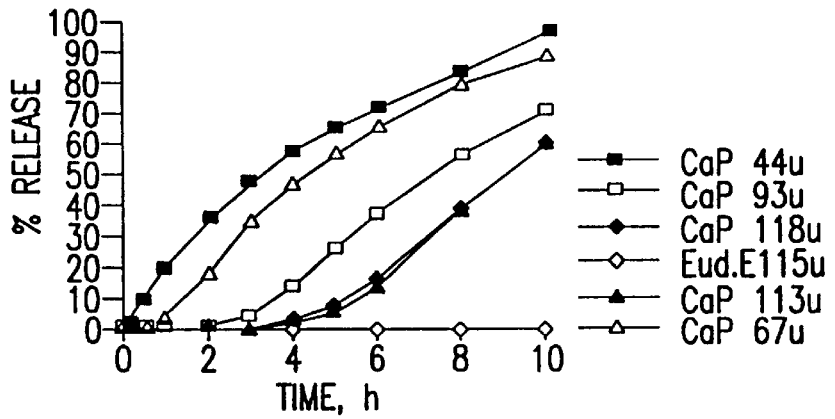
FIG. 4. Sodium salicylate release from calcium pectinate/pectin cores coated with Eudragit E™/calcium pectinate (1:1) films.

FIG. 4 shows the release of sodium salicylate from tablets coated with Eudragit E™/calcium pectinate (1:1). A film of 44μ was completely penetrable while a film of 67μ allowed transfer after a lag time of one hour. Release was then similar to that obtained with no coating. Films of 93μ and 115μ prevented release from the tablets for two and four hours respectively and retarded release thereafter.

Figure 5:
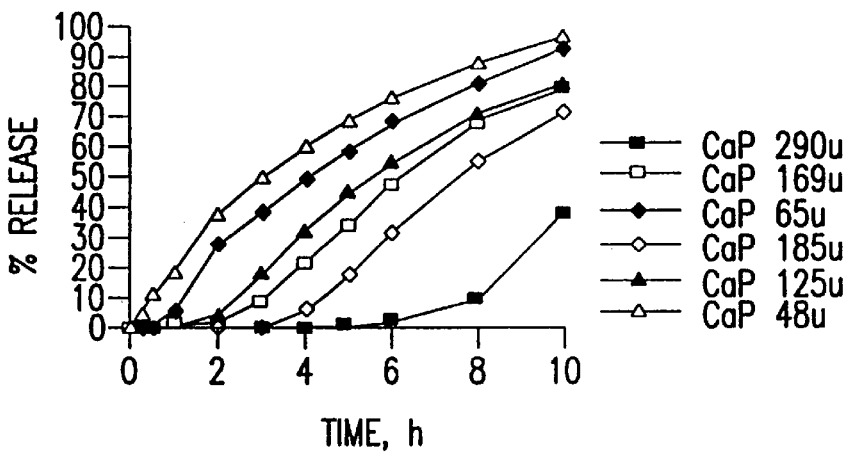
FIG. 5. Sodium salicylate release from calcium pectinate/pectin cores coated with Eudragit E™/calcium pectinate (3:7) films.

FIG. 5 shows release of sodium salicylate from tablets coated with Eudragit E™/calcium pectinate (3:7). There was no lag time with a film of 48μ and a lag time of one hour with a film of 65μ. The release of sodium salicylate was then similar to release with a non-coated tablet. Films of 125μ, 169μ, 185μ and 290μ delayed release 1, 2, 3, and 6 hours respectively. The subsequent release was retarded compared to a non-coated tablet.

Table 1 shows the collected data and the effect of % calcium pectinate on release of sodium salicylate from films of similar thickness.

TABLE 1

Effect of Percent Calcium Pectinate (% Calcium Pectinate) on Release of Sodium Salicylate

| Film Thickness (μ) | % Calcium Pectinate | % release- 2 hours | % release- 4 hours | % release- 6 hours |
|---|---|---|---|---|
| 74 | 0 | 0 | 0 | 0 |
| 60 | 30 | 1 | 3 | 10 |
| 67 | 50 | 18 | 40 | 60 |
| 65 | 70 | 25 | 48 | 65 |
| 115 | 0 | 0 | 0 | 0 |
| 118 | 50 | 0 | 2 | 10 |
| 125 | 70 | 3 | 28 | 40 |
| 290 | 70 | 0 | 0 | 3 |

The data in the table show clearly that increasing calcium pectinate leads to increasing rates of release of the soluble drug through the film.

The Effect of Calcium Pectinate Particle Size on the Release of Sodium Salicylate from Eudragit E™/Calcium Pectinate Films The calcium pectinate powder used to make the Eudragit™E/calcium pectinate films was fractionated by sieving into four fractions: <44μ, 44–74μ, 74–149μ, and >149μ. These fractions were designated A, B, C, and D, respectively. Eudragit E™/calcium pectinate films (3:7) were coated on tablets of sodium salicylate in a calcium pectinate/pectin matrix with each of the particle size fractions. The release of sodium salicylate was measured for each of these systems and the results are shown graphically in FIGS. 6–9.

Figure 6:
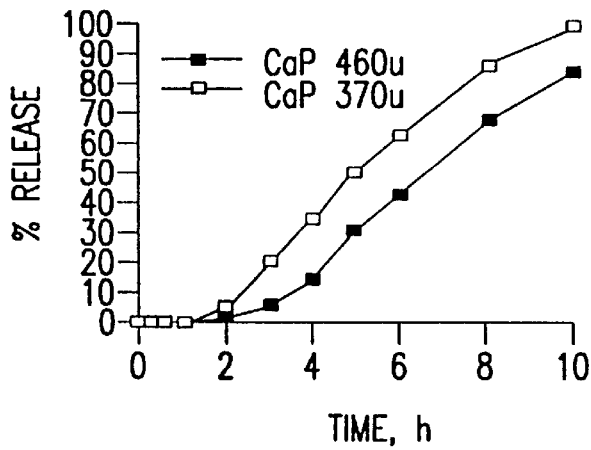
FIG. 6. Sodium salicylate release from calcium pectinate/pectin cores coated with Eudragit E™/calcium pectinate (3:7) films made from fraction A.

FIG. 6 shows the release of sodium salicylate from tablets coated with fraction A (<44μ). Films of 370–460μ cause a two-hour lag time and retarded release of the sodium salicylate thereafter.

Figure 7:
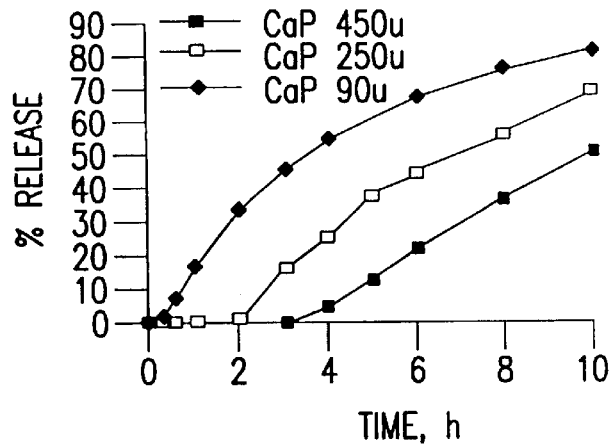
FIG. 7. Sodium salicylate release from calcium pectinate/pectin cores coated with Eudragit E™/calcium pectinate (3:7) films made from fraction B.

FIG. 7 shows the results of coating with fraction B. A film of 450μ causes a three-hour lag time and a film of 250μ causes a two-hour lag time.

Figure 8:
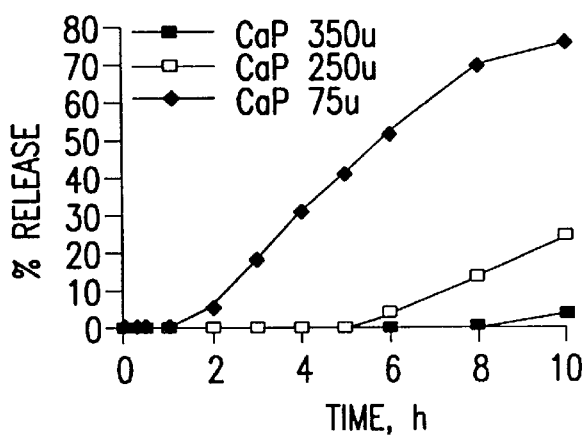
FIG. 8. Sodium salicylate release from calcium pectinate/pectin cores coated with Eudragit E™/calcium pectinate (3:7) films made from fraction C.

FIG. 8 shows the release of sodium salicylate from tablets coated with Eudragit E™/calcium pectinate using fraction C. A film of 250μ thickness causes a five-hour delay in the onset of drug release. A film of 350μ prevents drug release for eight hours.

Figure 9:
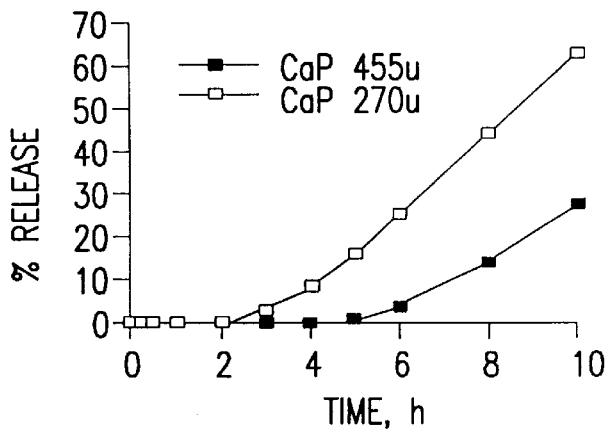
FIG. 9. Sodium salicylate release from calcium pectinate/pectin cores coated with Eudragit E™/calcium pectinate (3:7) films made from fractions A, B, and C.

FIG. 9 shows the release of sodium salicylate from tablets coated with a mixture of fractions A, B, and C in the ratio as originally synthesized. The results are intermediary to the data in the previous graphs. A film of 270μ causes a lag time of about three hours.

Table 2 is a collection of data from FIGS. 6–8. It shows the effect of the fraction size on the release of sodium salicylate from the matrix tablets at various film thicknesses. The smaller the particle size, the more quickly soluble drug is released.

TABLE 2

Release of Sodium Salicylate from Eudragit E ™/Calcium Pectinate (3:7) Coated Tablets as a Function of Calcium Pectinate Particle Size

| Film Thickness (μ) | Fraction | % release- 2 hours | % release- 4 hours | % release- 6 hours |
|---|---|---|---|---|
| 250 | 44–74μ | 0 | 15 | 40 |
| 250 | 74–149μ | 0 | 0 | 4 |
| 370 | <44μ | 3 | 35 | 60 |
| 350 | 74–149μ | 0 | 0 | 0 |
| 460 | <44μ | 1 | 12 | 40 |
| 450 | 44–74μ | 0 | 4 | 20 |

EXAMPLE 2

Eudragit E™/Calcium Pectinate Films versus Eudragit E™/Pectin Films

Figure 10:
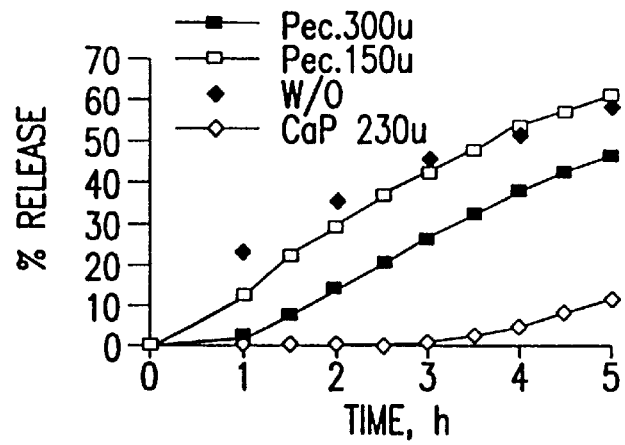
FIG. 10. Sodium salicylate release from calcium pectinate/pectin cores coated with Eudragit E™/calcium pectinate (3:7) films and Eudragit E™/pectin films.

A comparison was made between the films containing calcium pectinate and a film made with pectin of the same particle size spread. The results are shown in FIG. 10. A Eudragit E™/pectin (3:7) film of 300μ caused a one-hour delay in drug release and gave a release profile thereafter that was identical to that of a non-coated tablet. The Eudragit E™/calcium pectinate film of 230μ caused a delay of three hours and a slower release rate than the non-coated tablet, thereafter.

EXAMPLE 3

Eudragit E™/Calcium Pectinate Films on a Disintegrating Tablet

Figure 11:
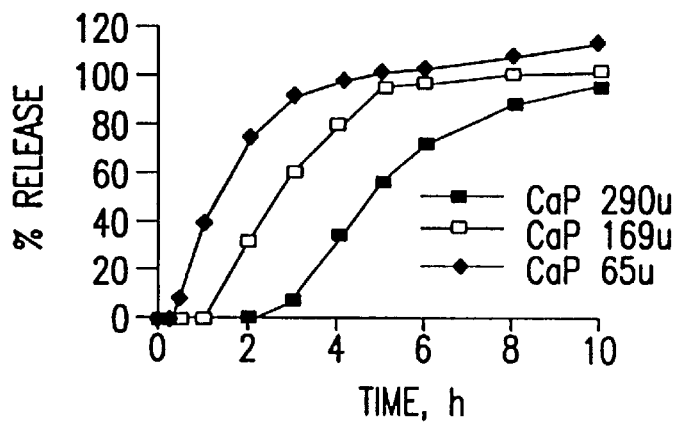
FIG. 11. Sodium salicylate release from microcrystalline cellulose cores coated with Eudragit E™/calcium pectinate (3:7).

Eudragit E™/calcium pectinate films (3:7) were coated onto an immediate-release tablet made of microcrystalline cellulose (Emcocel). The tablets contained 30 mg sodium salicylate, were 9 mm in diameter, and had a total weight of 250 mg. The films were capable of preventing disintegration of the tablets for various time intervals depending on film thickness. Films of Eudragit E™ alone prevented disintegration for over six hours (data not shown). The Eudragit E™/calcium pectinate (3:7) films delayed the onset of disintegration for up to three hours for films up to 300μ. The dissolution data on these coated tablets is shown in FIG. 11.

EXAMPLE 4

Figure 12:
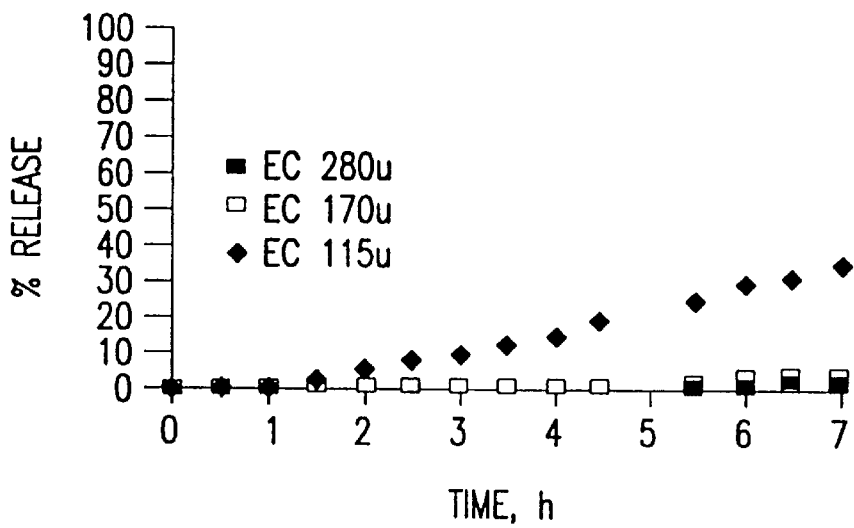
FIG. 12. Sodium salicylate release from calcium pectinate/pectin cores coated with ethylcellulose/calcium pectinate (3:7).
Figure 13:
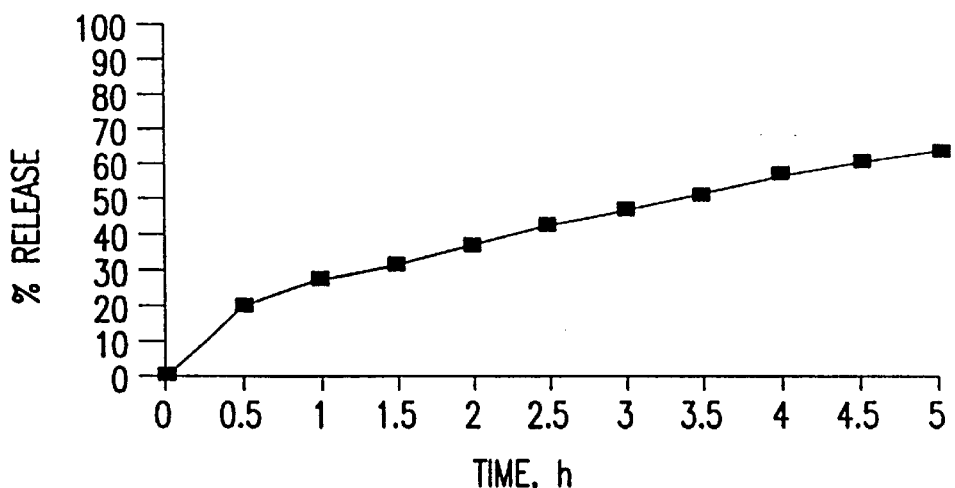
FIG. 13. Sodium salicylate release from calcium pectinate/pectin cores without coating.

Ethylcellulose as the Hydrophobic Film - Calcium Pectinate as Hydrophilic Particulate Tablets of 30 mg of sodium salicylate in a calcium pectinate/pectin matrix were coated with ethylcellulose. A coating thickness of 40μ was sufficient to totally seal the tablet from drug release for more than ten hours. The same tablets were coated with ethylcellulose/calcium pectinate (3:7) at various thicknesses. FIG. 12 shows the results of coating at thicknesses between 100μ and 300μ. A coating of 115μ prevented drug release for two hours after which the sodium salicylate was released in a zero order fashion at a slow controlled rate. The non-coated core is presented for comparison in FIG. 13. Without the coating, the cores released about 30% of the sodium salicylate in the first two hours and approximately 50% in five hours.

Figure 14:
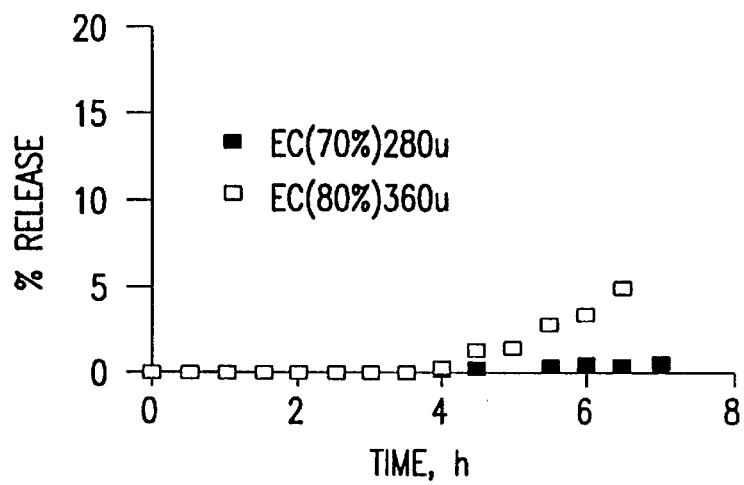
FIG. 14. Sodium salicylate release from calcium pectinate/pectin cores coated with ethylcellulose/calcium pectinate (3:7) or with ethylcellulose/calcium pectinate (2:8).

The calcium pectinate/pectin tablets mentioned above were coated with ethylcellulose/calcium pectinate at the ratio of 80% calcium pectinate instead of 70%. FIG. 14 shows that by raising the percentage of the hydrophilic particulate, the amount of time the device will prevent drug release can be controlled. With 70% calcium pectinate there was no drug release for seven hours (thickness of 280μ). With 80% calcium pectinate, there was drug release after five hours (thickness of 360μ).

EXAMPLE 5

Eudragit RS™ as Hydrophobic Film - Calcium Pectinate as Hydrophilic Particulate

Figure 15:
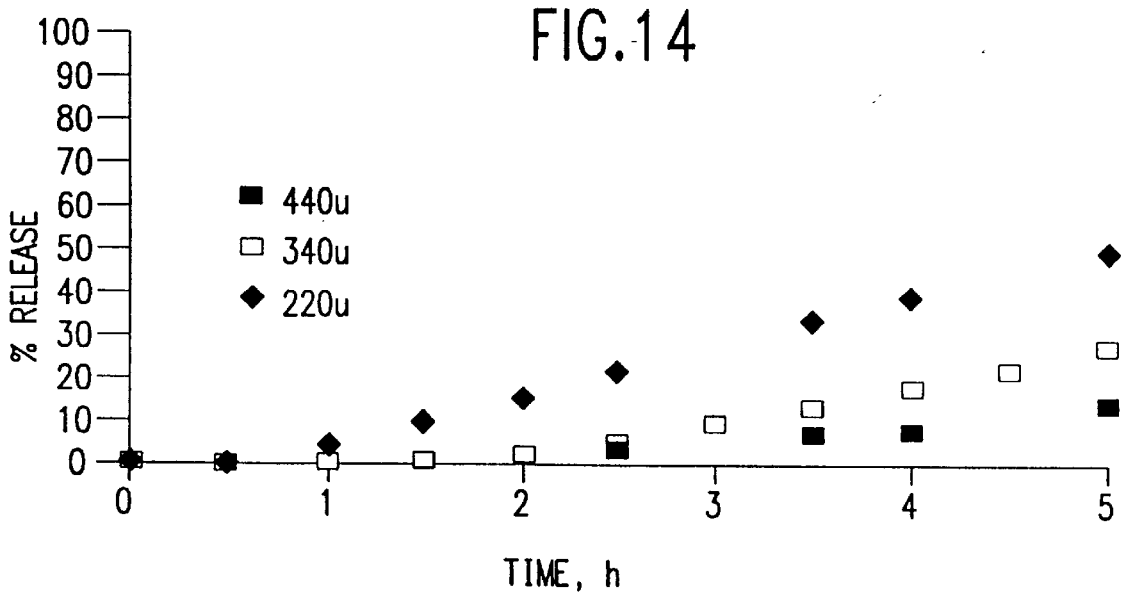
FIG. 15. Sodium salicylate release from calcium pectinate/pectin cores coated with Eudragit RS™/calcium pectinate (3:7).

Tablets containing 30 mg sodium salicylate in a calcium pectinate/pectin matrix were coated with Eudragit RS™/calcium pectinate (3:7) in the same manner as with Eudragit E™ and ethylcellulose. The results of dissolution tests for different thicknesses of coating are shown in FIG. 15. This polymer prevented drug release for two hours with a coating thickness of 440μ. Drug release was prevented for 1.5 hours with a coating thickness of 340μ. Drug release was prevented for 0.5 hours with a coating thickness of 220μ. While the absolute coating thickness varies from hydrophobic polymer to polymer, this experiment, along with the previous ones, shows that the controlled release of the drug can be achieved by varying the hydrophobic polymers.

EXAMPLE 6

Eudragit E™ as Hydrophobic Film - Crosslinked Byco as Hydrophilic Particulate

Figure 16:
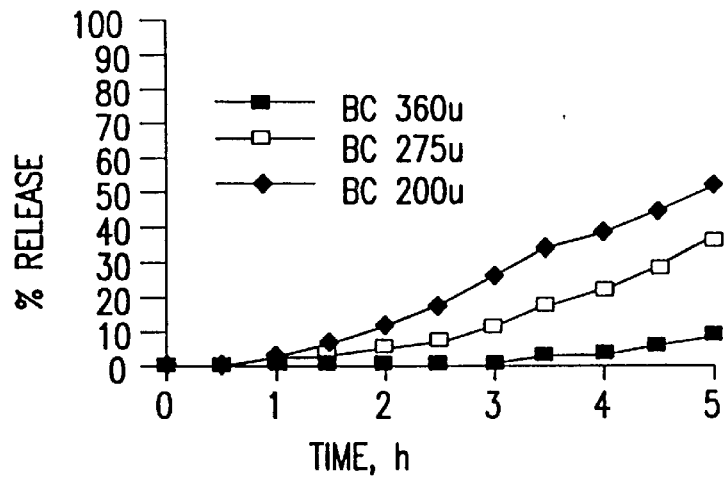
FIG. 16. Sodium salicylate release from calcium pectinate/pectin cores coated with Eudragit E™/crosslinked Byco (3:7).

Tablets containing 30 mg sodium salicylate in a calcium pectinate/pectin matrix were coated with Eudragit E™/crosslinked Byco (3:7) in the same manner as above. Films of Eudragit E™ alone completely prevented drug release from the tablet for at least seven hours. FIG. 16 shows the release obtained with a crosslinked protein (hydrolyzed gelatin crosslinked with gutaraldehyde and ground to a power) as the hydrophilic insoluble particulate. Films of 200μ thickness prevented drug release for approximately one hour. Those of 360μ prevented drug release for three hours.

EXAMPLE 7

Eudragit E™ as Hydrophobic Film - Crospovidone as Hydrophilic Particulate

Figure 17:
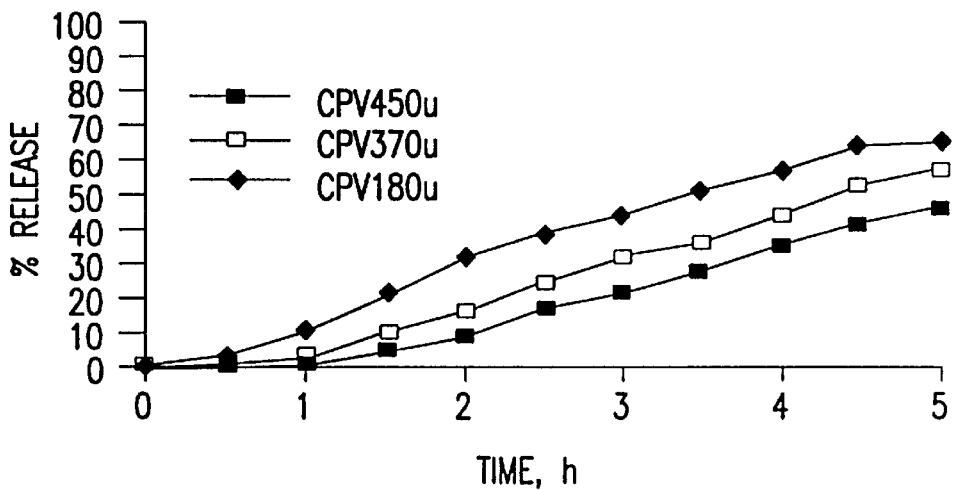
FIG. 17. Sodium salicylate release from calcium pectinate/pectin cores coated with Eudragit E™/Crospovidone (3:7).
Figure 18:
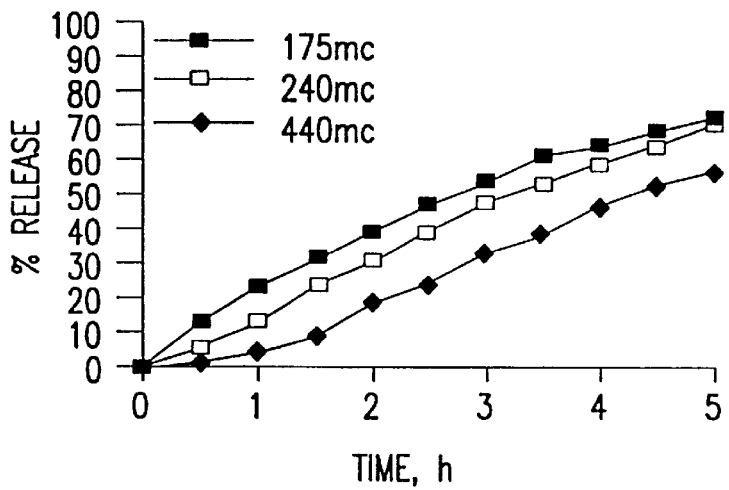
FIG. 18. Sodium salicylate release from calcium pectinate/pectin cores coated with Eudragit E™/Crospovidone (1:1)
Figure 19:
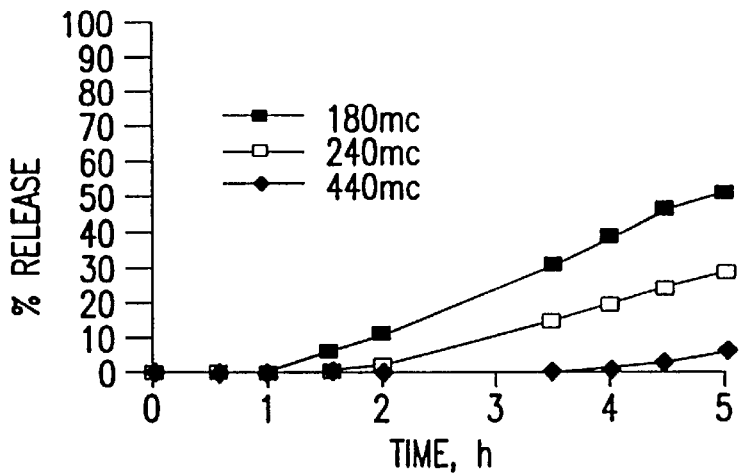
FIG. 19. Sodium salicylate release from calcium pectinate/pectin cores coated with Eudragit E™/Crospovidone (7:3).

Tablets containing 30 mg sodium salicylate in a calcium pectinate/pectin matrix were coated with of Eudragit E™/Crospovidone in ratios of 3:7, 1:1 and 7:3 in the same manner as above. Results of drug release in dissolution experiments are shown in FIGS. 17–19. With 70% and 50% Crospovidone, the release of the drug began the first hour. The tablet with the 180μ coating behaved similarly to the non-coated tablet. Thicker coatings caused delays in release of about one hour. Release profiles were more sustained than with an uncoated tablet. Coatings containing only 30% Crospovidone showed delays in release from one to four hours.

EXAMPLE 8

Figure 20:
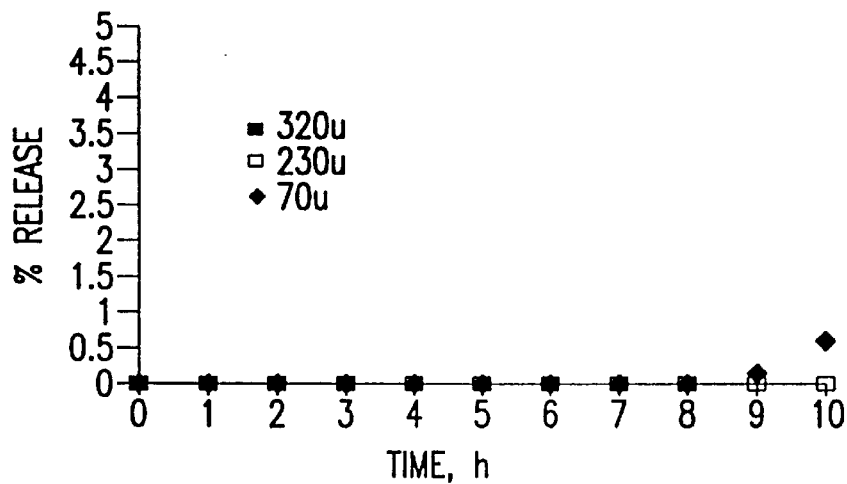
FIG. 20. Sodium salicylate release from calcium pectinate/pectin cores coated with Eudragit E™/microcrystalline cellulose (7:3).

Eudragit E™ as Hydrophobic Film - Microcrystalline Cellulose as Hydrophilic Particulate Tablets containing 30 mg sodium salicylate in a calcium pectinate/pectin matrix were coated with Eudragit E™ containing microcrystalline cellulose (Avicel) as the hydrophilic, water-insoluble particulate at levels of 30% and 70%. FIG. 20 shows the results of the dissolution test on tablets coated with a 7:3 ratio of Eudragit E™ to Avicel.

Figure 21:
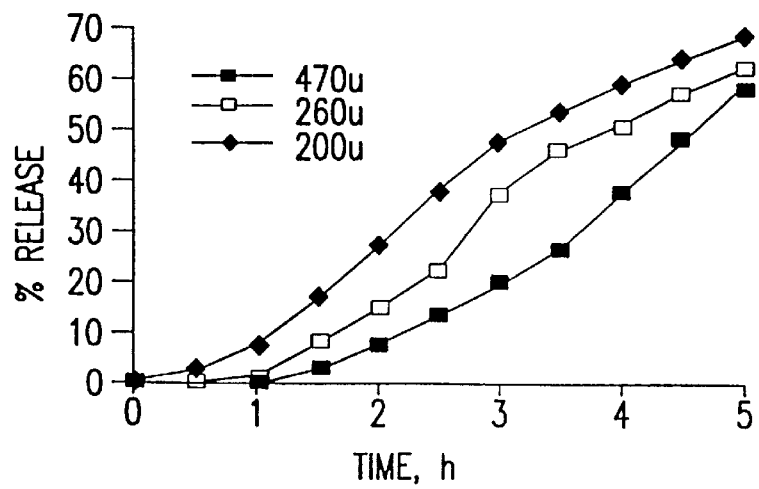
FIG. 21. Sodium salicylate release from calcium pectinate/pectin cores coated with Eudragit E™/microcrystalline cellulose (3:7).
Figure 21A:
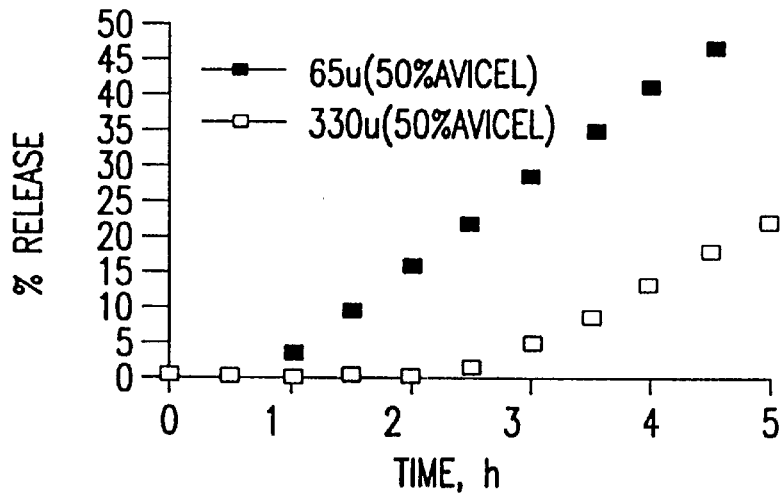
FIG. 21a. Sodium salicylate release from calcium pectinate/pectin cores coated with Eudragit E™/microcrystalline cellulose (1:1).

The coating with only 30% Avicel allows drug release only after nine hours (film thickness of 70μ). FIG. 21 shows the results of a dissolution study on the same tablets coated with a ratio of Eudragit E™/microcrystalline cellulose of 3:7. When 70% of the film is the hydrophilic particulate, drug release occurs more rapidly. A 260μ film caused a delay of an hour and controlled release thereafter. As has been shown in the other examples herein, an intermediate value of particulate content results in intermediate drug release values. FIG. 21a shows the results of release with a film of Eudragit E™/microcrystalline cellulose (1:1). When 50% of the weight of the film is the hydrophilic particulate, there is a two hour delay in drug release (330μ) with zero order release thereafter.

EXAMPLE 9

Figure 22:
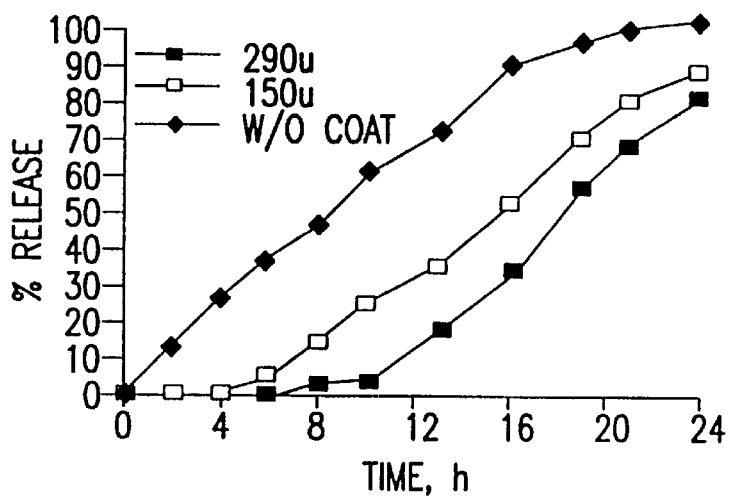
FIG. 22. Sodium diclofenac release from calcium pectinate/pectin cores coated with Eudragit E™/calcium pectinate (3:7).

Eudragit E™ as Hydrophobic Film - Calcium Pectinate as Hydrophilic Particulate, with 100 mg Sodium Diclofenac as Drug Marker A sustained release formulation containing 100 mg of sodium diclofenac in a calcium pectinate/pectin matrix was developed. The non-coated tablets showed close to zero order sustained release of the drug into intestinal TS over 16 hours. Coating the tablets with Eudragit E™/calcium pectinate (3:7) at thicknesses between 150μ and 290μ resulted in controlled delay of drug delivery for 4 to 6 hours. This time is sufficient for the drug to pass the small intestine and enter in the colon. The results of the dissolution tests on these formulations are shown in FIG. 22.

DISCUSSION OF EXEMPLARY MATERIAL

Particles of calcium pectinate in a film of Eudragit E™ are capable of dramatically altering the properties of the Eudragit E™ barrier film and give a new dimension to the control of release of soluble drugs from a matrix. A hydrogel matrix and a disintegrating tablet are incapable of total protection and targeting of soluble drugs which can diffuse out through the swollen hydrogel. With sodium salicylate as a soluble drug marker, the calcium pectinate/pectin matrix allowed up to 50% of the drug to diffuse out in four hours in intestinal TS.

To allow for targeted delivery of soluble drugs a barrier to diffusion is necessary. This barrier must allow for control over the release of the soluble drug to a timed point so that little or no drug is released before desired. The combination of non-water-soluble, but hydrophilic, particles in a hydrophobic coating allows for control of water entry into the tablet and diffusion of drug from the tablet. It has been shown that controlling several parameters (the percent of the particles, the particle size, the film thickness, the identity of the polymer, and the identity of the particulate material), the time and release profile of soluble drug from both a controlled delivery hydrogel tablet and an immediate delivery disintegrating tablet can be controlled. The general trend is as follows:

1. Percent of particles: The higher the percent of hydrophilic, non-soluble particulates embedded in the hydrophobic polymer, the earlier the release of the drug. This is thought to be because more channels are formed through which the soluble drug can diffuse.
2. Particle size of the particle: The smaller the particle size, the faster the release of drug for a given percent of particles. The smaller particles means that there are numerically more particles for a given weight percentage. The particles also have a larger total surface area so that more interaction among the particles embedded in the film is possible, possibly leading to more channels for drug delivery.

3. Film thickness: The thicker the film, the slower the release of the soluble drug. Thicker films require a longer time for swelling of the hydrophilic insoluble particles across the entire cross section of the hydrophobic barrier film.

4. Identity of the polymer and particulate: The more hydrophobic the polymer, the longer the release time when all other parameters are kept the same. It will take longer for the hydrophilic channels to form when the polymer is more hydrophobic. The more hydrophilic and swellable the particulate, the faster the release when all other parameters are kept the same, since the drug is released through the swollen hydrophilic channels. The more the particulate swells, the larger the channels. The more hydrophilic the particulate, the faster the channels form and the more efficient they are at allowing the drug to diffuse through them.

It is important to have many parameters that allow control of release of a drug since each drug-matrix combination is unique with a solubility profile of the drug and a diffusion profile of the matrix. The present invention allows one to tailor the design of the film coating to the needs of any system.

It has been shown that the drug delivery system herein, based on a non-soluble hydrophilic particulate embedded in a hydrophobic film, can be made of several different materials that meet the requirements. The non-soluble hydrophilic particulate can be calcium pectinate (a non-soluble metal salt of the polysaccharide pectin), glutaraldehyde-crosslinked hydrolyzed gelatin (Byco) (a non-soluble protein derivative), microcrystalline cellulose (an insoluble polysaccharide) and Crospovidone (a non-soluble crosslinked synthetic hydrophilic polymer). The hydrophobic film can be Eudragit E™ (an amino polymethacrylic acid), Eudragit RS™ (a quaternary ammonium polymethacrylic acid) or ethylcellulose (a derivative of the polysaccharide cellulose). The system has been shown to be viable on a hydrogel core (calcium pectinate/pectin) with 10% drug loading, a hydrogel core with 33% drug loading (sodium salicylate and sodium diclofenac) and on a disintegrating core (microcrystalline cellulose). These examples show the versatility of the system.

Having now fully described the invention, it would be understood by those with skill in the art that the invention may be performed within a wide and equivalent range of conditions, parameters, and the like, without affecting the spirit or scope of the invention or any embodiment therefore. All references cited herein are incorporated herein fully by reference for their relevant teachings.

What is claimed is:

1. A drug delivery formulation for localized drug release in the gastrointestinal tract of an animal comprising:
  a. a core comprising a drug and core material; and
  b. a coating surrounding said core, said coating having an outer surface,
    wherein said coating comprises water-insoluble hydrophilic particulate matter embedded in a water-insoluble carrier, such that when said formulation enters the gastrointestinal tract, said particulate matter absorbs liquid, thus forming channels that interconnect said core with said outer surface of said coating, and through which channels, said drug from said core is released into the gastrointestinal tract.

2. The formulation of claim 1 wherein said core is selected from the group consisting of tablets, capsules, and pellets.

3. The formulation of claim 1 wherein said water-insoluble carrier of said coating is selected from the group consisting of a dimethylaminoethylacrylate/ethylmethacrylate copolymer, said copolymer based on acrylic and methacrylic acid esters with a low content of quaternary ammonium groups, wherein the molar ratio of the ammonium groups to the remaining neutral (meth) acrylic acid esters is approximately 1:20, said polymer corresponding to USP/NF "Ammonio Methacrylate Copolymer Type A", an ethylmethacrylate/chlorotrimethylammoniumethyl methacrylate copolymer, said copolymer based on acrylic and methacrylic acid esters with a low content of quaternary ammonium groups wherein the molar ratio of the ammonium groups to the remaining neutral (meth)acrylic acid esters is 1:40, said polymer corresponding to USP/NF "Ammonio Methacrylate Copolymer Type B", a dimethylaminoethylmethacrylate/methylmethacrylate and butylmethacrylate copolymer, a copolymer based on neutral methacrylic acid esters and dimethylaminoethyl methacrylate esters wherein the polymer is cationic in the presence of acids, an ethylacrylate and methylacrylate/ethylmethacrylate and methyl methylacrylate copolymer, said copolymer being a neutral copolymer based on neutral methacrylic acid and acrylic acid esters, ethylcellulose, shellac, zein, and waxes.

4. The formulation of claim 1 wherein said coating (b) is further coated with an enteric coating.

5. The formulation of claim 1 wherein said core comprises a swellable material.

6. The formulation of claim 5 wherein said swellable material is selected from the group consisting of polysaccharide, cross-linked polyacrylic acid, and modified cellulose.

7. The formulation of claim 6 wherein said polysaccharide is selected from the group consisting of alginate, pectin, xantham gum, guar gum, carrageenan, tragacanth gum, locust bean gum, starch, microcrystalline starch, microcrystalline cellulose, metal salts thereof, and covalently crosslinked derivatives thereof.

8. The formulation of claim 6 wherein said modified cellulose is selected from the group consisting of hydroxypropylcellulose, hydroxyethylcellulose, hydroxypropylmethylcellulose and carboxymethylcellulose.

9. The formulation of claim 1 wherein said particulate matter comprises a polymer selected from the group consisting of a water-insoluble polysaccharide, a water-insoluble cross-linked polysaccharide, a water-insoluble polysaccharide metal salt, a water-insoluble cross-linked protein, a water-insoluble cross-linked peptide, water insoluble protein: polysaccharide complex, a water insoluble peptide: polysaccharide complex, a polysaccharide or a protein or peptide rendered insoluble by interaction with a poly-cation or poly-anion and a water-insoluble cross-linked hydrophilic polymer in dried powder form.

10. The formulation of claim 9 wherein said polysaccharide is selected from the group consisting of an insoluble metal salt of pectin, xantham gum, carrageenan, tragacanth gum, locust bean gum, and alginic acid; an insoluble crosslinked derivative of xantham gum, guar gum, dextran, carrageenan, tragacanth gum, locust bean gum, pectin, starch, hydroxypropylcellulose, hydroxyethylcellulose, hydroxypropylmethylcellulose, carboxymethylcellulose and alginic acid, cellulose, microcrystalline cellulose, insoluble starch and microcrystalline starch.

11. The formulation of claim 10 wherein said insoluble metal salt of alginic acid is selected from the group consisting of calcium alginate, zinc alginate, aluminum alginate, ferric alginate, and ferrous alginate.

12. The formulation of claim 10 wherein said insoluble metal salt of pectin is selected from the group consisting of calcium pectinate, zinc pectinate, aluminum pectinate, ferric pectinate, and ferrous pectinate.

13. The formulation of claim 9 wherein said cross-linking is by a cross-linking agent selected from the group consisting of formaldehyde, glutaraldehyde, epichlorhydrin, diacid chloride, diacid anhydride, diisocyanates, diamines and borax.

14. The formulation of claim 9 wherein said water insoluble cross-linked protein is selected from the group consisting of glutaraldehyde-cross-linked hydrolyzed gelatin, formaldehyde-cross-linked hydrolyzed gelatin, glutaraldehyde-cross-linked gelatin, formaldehyde-cross-linked gelatin, glutaraldehyde-cross-linked collagen and formaldehyde-cross-linked collagen.

15. The formulation of claim 9 wherein said water-insoluble cross-linked hydrophilic polymer is selected from the group consisting of carbomers.

16. The formulation of claim 9 wherein said water-insoluble cross-linked hydrophilic polymer is selected from the group consisting of Crospovidone.

17. The device of claim 1 wherein said water-insoluble carrier is a dimethylaminoethylmethacrylate/methylmethacrylate and butylmethacrylate copolymer, said copolymer based on neutral methacrylic acid esters and dimethylaminoethyl methacrylate esters, wherein said polymer is cationic in the presence of acids, said water-insoluble hydrophilic particulate is calcium pectinate, and said enteric coating is an anionic copolymer based on methacrylic acid and methylmethacrylate wherein the ratio of free carboxyl groups to the ester groups is approximately 1:1.

18. A method of delivering an agent to the gastrointestinal tract of a patient in need of such drug, wherein said method comprises oral administration of the drug delivery formulation of any of one of claims 1–17.

19. The method of claim 18 wherein said agent is selected from the group consisting of diagnostic and therapeutic agents.

20. The method of claim 18 wherein the portion of the gastrointestinal tract wherein said drug is released is selected from the group consisting of the stomach, the small intestine, the colon, and the rectum.

21. The method of claim 18 wherein said patient is treated for a disease selected from the group consisting of colitis, Crohn's disease, irritable bowel syndrome, gastritis, pancreatitis, hypertension, angina, arthritis, rheumatoid arthritis, asthma, arrythmia, local spasmolytic action, ulceration of the mucosa, diarrhea, constipation, polyps, carcinoma, cysts, infectious disorders, and parasitic disorders.

* * * * *